(12) United States Patent
Rosazza et al.

(10) Patent No.: US 7,112,573 B2
(45) Date of Patent: Sep. 26, 2006

(54) ISOFLAVONE AND TRITERPENE GLYCOSIDES FROM SOYBEANS

(75) Inventors: John P. N. Rosazza, Iowa City, IA (US); Mohammed Hosny, Makrum Abid-Nasr (EG)

(73) Assignee: Iowa Research, The University Foundation, Iowa City, IA (US)

( * ) Notice: Subject to any disclaimer, the term of this patent is extended or adjusted under 35 U.S.C. 154(b) by 375 days.

(21) Appl. No.: 10/126,483

(22) Filed: Apr. 19, 2002

(65) Prior Publication Data

US 2003/0203856 A1 Oct. 30, 2003

(51) Int. Cl.
*A01N 43/04* (2006.01)
*A61K 31/70* (2006.01)
*C07H 15/00* (2006.01)
*C07H 17/00* (2006.01)

(52) U.S. Cl. ............................. 514/27; 536/4.1; 536/8
(58) Field of Classification Search ................ 536/4.1, 536/8; 514/27
See application file for complete search history.

(56) References Cited

U.S. PATENT DOCUMENTS

| 3,070,623 A | 12/1962 | Gottfried et al. | 260/468.5 |
|---|---|---|---|
| 3,070,624 A | 12/1962 | Baxendale et al. | 260/468.5 |
| 4,524,067 A | 6/1985 | Arichi et al. | 514/33 |
| 5,182,373 A | 1/1993 | Kim et al. | 536/4.1 |
| 5,952,374 A * | 9/1999 | Clarkson et al. | 514/456 |
| 6,080,725 A | 6/2000 | Marciani | 514/26 |

FOREIGN PATENT DOCUMENTS

| BE | 753773 | 12/1970 |
|---|---|---|
| GB | 1346871 | 2/1974 |
| JP | A-4432798 | 12/1969 |
| JP | 2001-72697 | 3/2001 |

OTHER PUBLICATIONS

Nikaido et al., "Inhibition of Adenosine 3',5'-Cyclic Monophosphate Phosphodiesterase by Flavonoids. III", Chemical and Pharmaceutical Bullitin, 37(5), pp. 1392-1395, 1989.*
Agrawal, "Carbon-13 NMR of Flavonoids," Elsevier Science: NY, Studies in Organic Chemistry, 39:192-211, 1989.
Akiyama et al., "Geinstein, a specific inhibitor of tyrosine-specific protein kinases," *J. Biol. Chem.*, 262(12):5592-5595, 1987.
Arao et al., "Oleanene-type triterpene glycosides from puerariae radix. IV six new saponins from Pueraria lobata," *Chem. Pharm. Bull.*, 45(2):362-366, 1997.
Choi et al., "Genistein-induced G2/M arrest is associated with the inhibition of cyclin B1 and the induction of P21 in human breast carcinoma cells," *Int. J. Oncol.*, 13(2):391-396, 1998.
Doll et al, "Clinical trial of a triterpenoid liquorice compound in gastric and duodenal ulcer," *Lancet* 1:793-796, 1962.
Harborne et al, *The Flavonoids*; Academic Press: NY, PT2:756-761, 1975.
Hawrylewicz et al, "Soy and experimental cancer: animal studies," *J. Nutr.*, 125:698S-708S, 1995.
Heinonen et al, "Identification of Isoflavone metabolites dihydrodaidzein, dihydrogenistein, 6'-OH-O-dma, and cis-4-OH-equol in human urine by gas chromatography—mass spectroscopy using authentic reference compounds," *Anal. Biochem.*, 274:211-219, 1999.
Herman et al., "Soybean phytoestrogen intake and cancer risk," *J. Nutr.*, 125:757S-770S, 1995.
Hosny and Rosazza, "Novel isoflavone, cinnamic acid, and triterpenoid glycosides in soybean molasses," *J. Nat. Prod.*, 62:853-858, 1999.
Huang et al., "Antitumor activity of total saponins from Dolichos falcatus Klein," *Zhongueo Yaoii Xuebao*, Chemical abstract No. 98:100885, 3:286-288, 1982, Journal in Chinese, English abstract provided.
Inoue et al., "Inhibitory effect of Glycyrrhetinic acid derivatives on lipoxygenase and prostaglandin synthetase," *Chem. Pharm. Bull.* 34(2):897-901, 1986.
Jing et al, "Differntiation of promyelocytic leukemia cells HL-60 induced by Daidzein in vitro and in vivo," *Anticancer Res.*, 13:1049-1054, 1993.
Joannou et al, "A urinary profile study of dietary phytoestrogens. The identification and mode metabolism of new isoflavonoids," *J. Steroid Biochem. Molec. Biol,.* 54(3/4):167-184, 1995.
Kashiwada et al., "Anti-tumor agents. 136[1]. Cumingianosides A-F, potent antileukemic new triterpene glucosides, and cumindysosides A and B, Trisnor- and Tetranortriterpene glucosides with a 14,18-Cycloapoeuphane-t/ype skeleton from Dysoxylum cumingianum," *J. Org. Chem.*, 57:6946-6953, 1992.
Kitagawa et al, "Characterization of saponin constituents in soybeans of various origins and quantitative analysis of soyasaponins by gas-liquid chromatography," *Yakugaku Zasshi*, 104:162-168, 1984, contains an English abstract.
Kitagawa et al, "Saponin and sapogenol. XXXVIII[1]. Structure of soyasaponin $A_2$, a bisdesmoside of soyasapogenol A, from soybean, the seeds of Glycine max MERILL," *Chem. Pharm. Bull.*, 33(2):598-608, 1985.
Kong et al., "Triterpeniod glycosides from Decaisnea Fargesii," *Phytochemistry*, 33(2):427-430, 1993.
Menon et al, "Effect of isoflavones genistein and daidzein in the inhibition of lung metastasis in mice induced by B16F-10 melanoma cells," *Nutr. Cancer,* 30:74-77, 1998.

(Continued)

*Primary Examiner*—Shaojia Anna Jiang
*Assistant Examiner*—Traviss McIntosh
(74) *Attorney, Agent, or Firm*—Fulbright & Jaworski L.L.P.

(57) ABSTRACT

The invention provides new isoflavonoid and triterpenoid compounds isolated from a soybean phytochemical concentrate. The new compounds have exhibited cytotoxic activity against selected tumor cell lines. Pharmaceutical compositions comprising the new compounds and methods for use thereof are provided by the invention.

5 Claims, 3 Drawing Sheets

OTHER PUBLICATIONS

Merz-Demlow et al, "Soy isoflavones improve plasma lipids in normocholesterolemic, premenopausal women," *Am. J. Clin. Nutr.*, 71:1462-1469, 2000.

Messina et al, "Soy intake and cancer risk: a review of the in vitro and in vivo data," *Nutr. Cancer*, 21:113-131, 1994.

Messina, "Legumes and soybeans: overview of their nutritional profiles and health effects," *Am. J. Clin. Nutr.*, 70(Suppl):439S-450S, 1999.

Nagamoto et al., "Antitumor constituents from bulbs of Crocosmia crocosmiiflora," *Planta Medica.*, 54:305-307, 1988.

Naik et al, "An in vitro and in vivo study of antitumor effects of genistein on hormone refractory prostate cancer," *Anticancer Res.*, 14:2617-2619, 1994.

Naim et al, "Antioxidative and antihemolytic activities of soybean isoflavones," *J. Agric. Food Chem.*, 24(6):1174-1177, 1976.

Nikaido et al., "Inhibition of adenosine 3'5'-cyclic monophosphate phosphodiesterase by flavonoids, III," *Chem. Pharm. Bull.*, 37(5): 1392-1395, 1989.

Nwokolo and Smartt, "Soybean (Glycine Max (L.) Merr.)," Chapter 8 In: *Food and Feed from Legumes and oilseeds:* Chapman and Hall: London, 90-102, 1996.

Okura et al, "Effect of genistein on topoisomerase activity and on the growth of [VAL 12] Ha-ras-transformed NIH 3T3 cells," *Biochem. Biophys. Res. Commun.*, 157:183-189, 1988.

Peterson and Barnes, "Genistein inhibition of the growth of human breast cancer cells: independence from estrogen receptors and the multi-drug resistance gene," *Biochem. Biophys. Res. Commun.*, 179:661-667, 1991.

Pisha et al., "Discovery of betulinic acid as a selective inhibitor of human melanoma that functions by induction of apoptosis," *Nature Medicine*, 1:1046-1051, 1995.

Pool-Zobel et al, "Isoflavonoids and linans have different potentials to modulate oxidative genetic damage in human colon cells," *Carcinogenesis*, 21(6):1247-1252, 2000.

Rao and Sung, "Saponins as anticarcinogens," *J. Nutr.*, 125:717S-724S, 1995.

Rao et al, "Enhancement of experimental colon cancer by genistein," *Cancer Res.*, 57:3717-3722, 1997.

Setchell, "Phytoestrogens: the biochemistry, physiology, and implications for human health of soy isoflavones[1,2]," *Am. J. Clin. Nutr.*, 68(Suppl):1333S-1346S, 1998.

Taniyama et al, "Saponin and sapogenol. XLIV.[1)] Soyasaponin composition in soybeans of various origins and soyasaponin content in various organs of soybean. Structure of Soyasaponin V form soybean hypocotyl," *Yakugaku Zasshi*, 108:562-571, 1988, contains an English abstract.

Tezuka et al, "Properties of tofus and soy milks prepared from soybeans having different subunits of glycinin," *J. Agric. Food Chem.*, 48:1111-1117, 2000.

Tomas-Barbaran et al., "A cytotoxic triterpenoid and flavonoids from crossopteryx febrigua," *Planta Medica.*, 54:266-267, 1988.

Yanagihara et al, "Antiproliferative effects of isoflavones on human cancer cell lines established from the gastrointestinal tract," *Cancer Res.*, 53:5815-5821, 1993.

Zhou et al, "Inhibition of murine bladder tumorigenesis by soy isoflavones via alterations in the cell cycle, apoptosis, and angiogenesis," *Cancer Res.*, 58:5231-5238, 1998.

Zhou et al, "Soybean phytochemicals inhibit the growth of transplantable human prostate carcinoma and tumor angiogenesis in mice," *J. Nutrit.*, 129:1628-1635, 1999.

\* cited by examiner

ISOFLAVONE AND TRITERPENE GLYCOSIDES FROM SOYBEANS

The government owns rights in the present invention pursuant to grant number 00-34188-9162 from the USDA Byproducts for Biotechnology Consortium.

BACKGROUND OF THE INVENTION

1. Field of the Invention

The present invention relates generally to the field of chemistry and oncology. More specifically, the invention relates to new compounds that were isolated from soybeans as well as methods for the use thereof

2. Description of Related Art

Numerous compounds isolated from plants have been investigated for biological properties. For example, triterpene saponins have been identified with fungicidal, antiviral, anti-mutagenic, spermicidal or contraceptive, cardiovascular, and anti-inflammatory activities (Hostettmann et al., 1995). Saponins are known to form complexes with cholesterol by binding plasma lipids, thereby altering cholesterol metabolism (Oakenfull et al., 1983). Triterpene glycosides given in feed also have been shown to decrease the amount of cholesterol in the blood and tissues of experimental animals (Cheeke, 1971).

Soybeans, and processed soy products containing isoflavonoids and saponins in particular are of wide interest for their multifaceted biological effects (Messina, 1999; Messina et al., 1994; Merz-Demlow et al., 2000; Setchell, 1998). Isoflavone, cinnamic acid and triterpenoid glycoside compounds have been isolated from soybean molasses, a concentrate of the aqueous extract prepared during the processing of soybeans (Hosny and Rosazza, 1999). A soybean phytochemical concentrate (SPC) comprising a powdered proprietary concentrate prepared from soybeans (*Glycine max* L. Merr.) has been described by Archer Daniel Midland Co. (Zhou et al., 1999). SPC contains 40–50% (w/w) of soy isoflavones with a profile of components that matches those found in tofu, the most commonly consumed soy food (Tezuka et al., 2000). The principal known isoflavones in SPC are daidzein-7-O-β-D-(6"-O-acetylglucopyranoside), and genistein-7-O-β-D-(6"-O-acetylglucopyrano-side) along with daidzein, genistein, glycitein and their respective β-glucosides daidzin, genistin and glycitin. While the overall composition of SPC is similar to that of soybean molasses, SPC also contains different isoflavonoid components (Hosny and Rosazza, 1999; Zhou et al., 1999) and soy saponins, plus a variety of very minor components, all of which are found naturally in soybeans.

Several investigations have shown that soy isoflavonoids, particularly genistein, inhibit the proliferation of transformed cells in culture (Arao et al., 1997) and some in vivo studies (Rao et al., 1997) report that pure isoflavones or dietary soy protein inhibit tumorigenesis in rodent models (Hawrylewicz et al., 1995). Genistein is a naturally occurring isoflavonoid isolated from soy products that is a known tyrosine kinase inhibitor shown to inhibit the proliferation of estrogen-positive and estrogen-negative breast cancer cell lines (Akiyama et al., 1987).

Different mechanisms may be implicated for such biological activities including: agonist/antagonist effects on estrogen receptors (Adlercreutz et al., 1995), stimulation of sex hormone-binding globulin synthesis (Adlercreutz et al., 1995), inhibition of growth factor-associated tyrosine-kinase signal transduction (Akiyama et al., 1987), antioxidant properties (Naim et al., 1976), and inhibition of DNA topoisomerase (Okura et al., 1988). Although such studies are highly suggestive of the beneficial effects of soy consumption in general with regard to cancer prevention, definitive intervention trials have not been completed. In contrast, others have shown that particular soybean components do not inhibit tumorigenesis (Messina et al., 1994). Consumption of a soybean-based diet (McIntosh et al., 1995) or administration of genistein (Rao et al., 1997) resulted in increasing colon tumor incidence and tumor burden in rats treated by chemical carcinogens. Further, it has been hypothesized that the estrogenic properties of certain soy isoflavones may stimulate breast tumor growth under some conditions (Peterson and Barnes, 1991)

One triterpene known to have biological activity is glycyrrhetinic acid. This compound and certain derivatives thereof have been shown to have anti-ulcer, anti-inflammatory, anti-allergic, anti-hepatitis and antiviral actions. For instance, certain glycyrrhetinic acid derivatives can prevent or heal gastric ulcers (Doll et al., 1962). Among such compounds known in the art are carbenoxolone (U.S. Pat. No. 3,070,623), glycyrrhetinic acid ester derivatives having substituents at the 3' position (U.S. Pat. No. 3,070,624), amino acid salts of glycyrrhetinic acid (Japanese Patent Publication JP-A-44-32798), amide derivatives of glycyrrhetinic acid (Belgian Patent 753773), and amide derivatives of 11-deoxoglycyrrhetinic acid (British Patent 1346871). Glycyrrhetinic acid has been shown to inhibit enzymes involved in leukotriene biosynthesis, including 5-lipoxygenase activity, and this is thought to be responsible for the reported anti-inflammatory activity (Inoue et al., 1986).

Betulinic acid, a pentacyclic triterpene, is reported to be a selective inhibitor of human melanoma tumor growth in nude mouse xenograft models and was shown to cause cytotoxicity by inducing apoptosis (Pisha et al., 1995). A triterpene saponin from a Chinese medicinal plant in the Cucurbitaceae family has demonstrated anti-tumor activity (Kong et al., 1993). Monoglycosides of triterpenes have been shown to exhibit potent and selective cytotoxicity against MOLT-4 human leukemia cells (Kasiwada et al., 1992) and certain triterpene glycosides of the Iridaceae family inhibited the growth of tumors and increased the life span of mice implanted with Ehrlich ascites carcinoma (Nagamoto et al., 1988). A saponin preparation from the plant *Dolichos falcatus*, which belongs to the Leguminosae family, has been reported to be effective against sarcoma-37 cells in vitro and in vivo (Huang et al., 1982). Soya saponin, also from the Leguminosae family, has been shown to be effective against a number of tumors (Tomas-Barbaren et al., 1988).

While previous studies have identified compounds which have any of a number of uses, there still is a great need in the art for the identification of novel biologically active compounds. Prior compounds may be toxic to normal cells or possess other undesirable characteristics or may have limited or varying degrees of biological activity. Therefore, identification of new compounds may provide new routes of treating a variety of conditions, thereby avoiding the shortcomings of the prior art.

SUMMARY OF THE INVENTION

The invention provides new isoflavonoid and triterpenoid compounds that were initially isolated from soybeans as well as methods for the use thereof. For example, in one aspect of the invention, a compound is provided represented by formula (I):

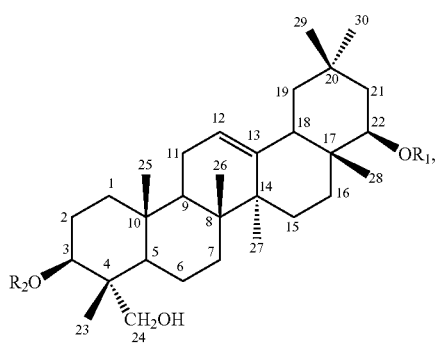

or pharmaceutically acceptable salts thereof, wherein $R_1$ is a disaccharide comprising sugars which are independently selected from the group consisting of arabinose, glucose and rhamnose; and wherein $R_2$ is a trisaccharide comprising sugars which are independently selected from the group consisting of glucuronic acid, galactose and glucose. In one embodiment of the invention, $R_1$ is represented by formula (II)

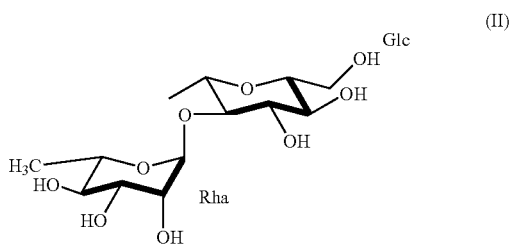

In yet another embodiment of the invention, $R_1$ is represented by formula (III)

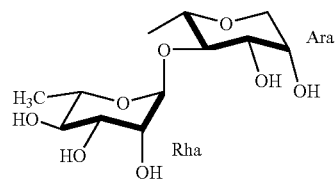

In a still further embodiment of the invention, $R_2$ is represented by formula (IV):

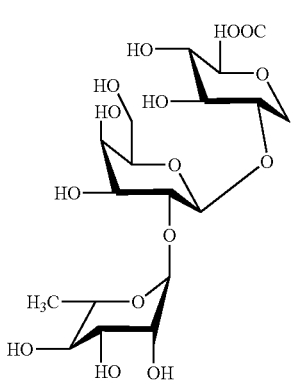

In another aspect of the invention, a compound is provided that is represented by formula (V):

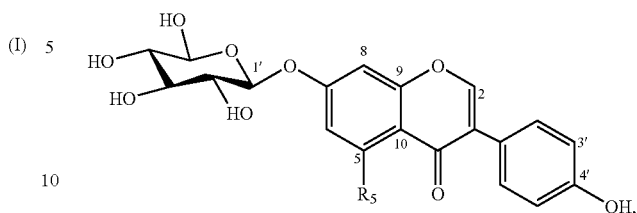

or a pharmaceutically acceptable salt thereof, wherein $R_5$ represents a hydrogen or hydroxyl. In certain embodiments of the invention, $R_5$ may be a hydrogen or hydroxyl.

In yet another aspect of the invention, a compound is provided represented by formula (VI):

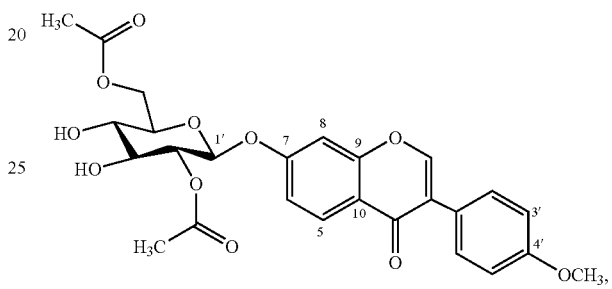

or a pharmaceutically acceptable salt thereof

In still yet another aspect of the invention, pharmaceutical compositions are provided which comprise one or more, including any possible combination thereof, of the compounds provided by the invention. Such a pharmaceutical composition may comprise a pharmacologically acceptable medium, for example, a buffer, a solvent, a diluent, an inert carrier, an oil, a creme, or an edible material. The pharmaceutical composition may be formulated, for example, in a tablet, capsule, topical preparation or dietary supplement.

In still yet another aspect, a. method is provided of inducing apoptosis in a cell comprising contacting said cell with a therapeutically effective amount of the pharmaceutical composition of claim 9. In one embodiment of the invention, the cell may be a mammalian cell, and/or a malignant cell, and may be further located in a human. In the method, contacting may comprise administering said pharmaceutical composition to a human. Such administration may be by any method, including oral, topical, intravenous, via intratumoral injection and by inhaling an aerosol. In certain embodiments of the invention, the cell is a skin cell, a colon cell, a uterine cell, an ovarian cell, a pancreatic cell, a prostate cell, a renal cell, a lung cell, a bladder cell or a breast cell. The method may further comprise administering at least a second pharmaceutical composition and/or may comprise irradiating the cell, for example, with X-ray radiation, UV-radiation, γ-radiation, or microwave radiation.

In still yet another aspect, the invention provides a method of treating a hyperproliferative disorder in a mammal comprising administering a therapeutically effective amount of a pharmaceutical composition of the invention to the mammal. Administering of the pharmaceutical composition may comprise administering more than one time. The mammal may be a human. In certain embodiments of the invention, administering is oral, topical, intravenous, via intratumoral injection, by inhaling an aerosol, by intratracheal injection, by intraperitoneal injection and/or by intravesical instillation, intra-arterial infusion, intrapericardial injection or intramuscular injection. The method may also comprise administering at least a second pharmaceutical composition. In one embodiment of the invention, the hyperproliferative disorder is cancer, including lung, head and neck, pancreatic, prostate, renal, bone, testicular, breast, cervical, gastrointestinal, lymphoma, brain, breast, ovarian, leukemia, myeloma, colorectal, esophageal, skin, thyroid, liver or bladder cancer. The cancer may comprise a tumor and the method may comprise irradiating the tumor. The method may further comprise irradiating a tumor cell, for example, with X-ray radiation, UV-radiation, γ-radiation, or microwave radiation.

In the method, the pharmaceutical composition may be administered to a tumor bed prior to and/or after resection of the tumor. In one embodiment of the invention, the pharmaceutical compositions is administered prior to or after chemotherapy, surgery, immunotherapy, hormonal therapy, or radiotherapy. In another embodiment of the invention, the hyperproliferative disease is rheumatoid arthritis, inflammatory bowel disease, osteo-arthritis, adenoma, leiomyoma, lipoma, hemangioma, fibroma, restenosis, pre-neoplastic lesions, vascular occlusion, or psoriasis.

In still yet another aspect of the invention, kit comprising the pharmaceutical compositions of the invention in a suitable container means are also provided.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein.

DESCRIPTION OF ILLUSTRATIVE EMBODIMENTS

Figure 1:
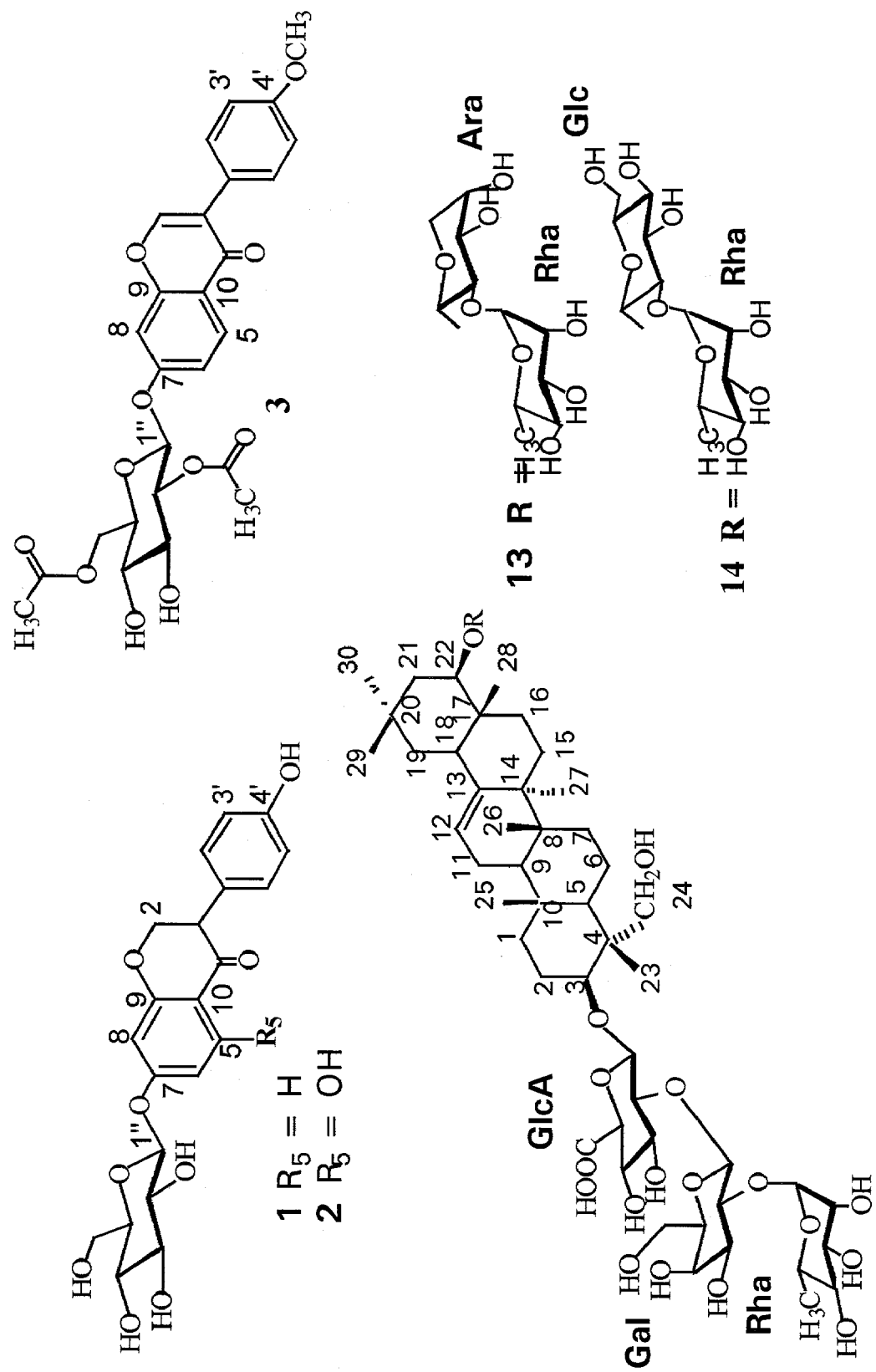
FIG. 1. Structures of new isoflavonoids and saponins isolated from soybean phytochemical extract.

The inventors have isolated and identified new isoflavonoid and triterpenoid components from a soybean phytochemical concentrate (SPC) (Zhou et al., 1999). Chemical investigation of a soybean phytochemical concentrate resulted in the identification of two new isoflavanones, dihydrodaidzin (designated herein compound "1") and dihydrogenistin (designated herein compound "2"), a new isoflavone, 2",6"-O-diacetyloninin (designated herein compound "3"), and two new triterpenoid saponins (designated herein compounds "13" and "14") (FIG. 1). The chemical structures of the new compounds were established by a combination of extensive NMR (DEPT, DQF-COSY, HMBC, HMQC and ROESY) studies and chemical degradation. The identification of the new compounds is significant in that several of the compounds were demonstrated to have cytotoxic activity against tumor cell lines.

Dihydrodaidzin (1) and dihydrogenistin (2) are previously undescribed isoflavone glycosides. The isoflavanone aglycones of 1 and 2 were previously identified as products of biotransformation by human intestinal bacteria. In the gut, the isoflavone glycosides daidzin (8) and genistin (9) are cleaved by intestinal glycosylases to daidzein (4) and genistein (5), and the aglycones are subsequently reduced by the gut microflora to form the free isoflavanone aglycones of 1 and 2 (Joannou et al., 1995; Heinonen et al., 1999). Although 1 was reported in the literature, no corresponding spectral data for this compound has been presented (Nikaido et al., 1989).

The new triterpenoid saponins provided by the invention are exemplified by the structure of formula (I):

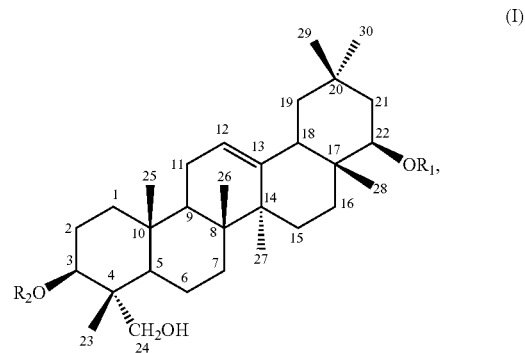

(I)

where $R_1$ is a disaccharide comprising sugars which are independently selected from the group consisting of arabinose, glucose and rhamnose; and wherein $R_2$ is a trisaccharide comprising sugars which are independently selected from the group consisting of glucuronic acid, galactose and glucose. In certain aspects of the invention, $R_1$ may be represented by formula (II) or formula (III), below:

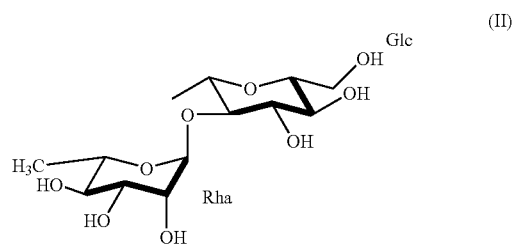

(II)

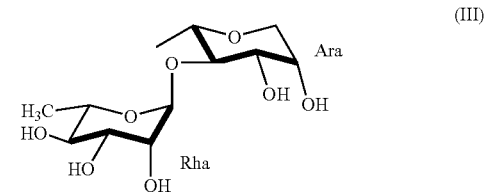

(III)

In certain further aspects of the invention, $R_2$ may be represented by formula (IV):

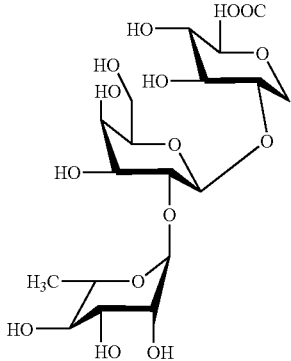

(IV)

Further provided by the invention are the new isoflavanones dihydrodaidzin and dihydrogenistin, for example, as given by formula (V):

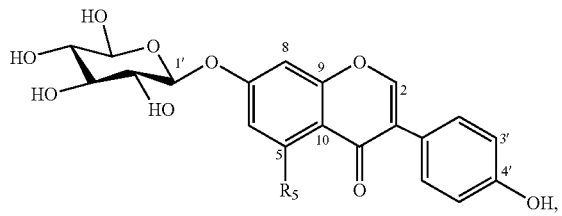

(V)

wherein $R_5$ represents a hydrogen or hydroxyl.

Still further provided by the invention is the new isoflavone, 2",6"-O-diacetyloninin, given, for example, in formula (VI):

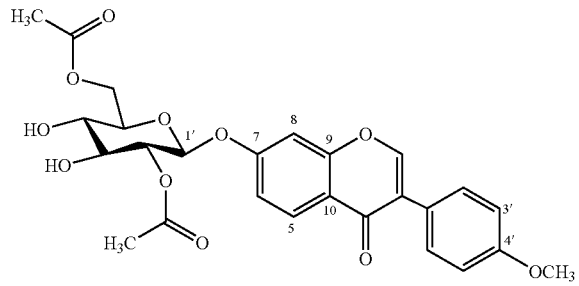

(VI)

I. Use of the New Isoflavonoid and Triterpene Saponin Compounds

Cytotoxic activities (ED50) of the new isoflavonoid and triterpene saponin compounds were measured against human stomach carcinoma (Hs 740.T, Hs 756 T), breast adenocarcinoma (Hs 578 T, Hs 742.T) and prostate carcinoma (DU 145, LNCaP-FGC) cell lines. Isoflavonoids 3 and 5 were found to be more active than 1 and 2 vs. at least one of the three cell lines examined, indicating the importance of the 2,3-double bond in cytotoxicity. Saponins 13, 14 and 15 were slightly more active than known saponins designated 16 and 17, indicating that sugar attachments at position-22 enhance cytotoxic activity. The results of the cytotoxicity assays indicate their potential as therapeutics for the prevention or treatment of hyperproliferative diseases including cancer. Techniques and considerations for such a use of the compounds are further discussed in detail herein below.

The inventors specifically contemplate further uses of the compounds of the invention for a range of applications in addition to the inhibition of tumor cell growth. For example, the compounds of the invention may, in certain aspects of the invention, find use as anti-fungal and anti-viral agents, piscicides or molluscicides, contraceptives, antihelmintics, UV-protectants, expectorants, diuretics, anti-inflammatory agents, regulators of cholesterol metabolism, cardiovascular effectors, anti-ulcer agents, analgesics, sedatives, immunomodulators and antipyretics.

The compounds of the invention may further find use in the regulation of angiogenesis. Angiogenesis or neovascularization is defined as the growth of new blood vessels. Tumors and cancers induce angiogenesis to provide a lifeline for oxygen and nutrients for the tumor to thrive. The development of new blood vessels also provide exits for malignant cancer cells to spread to other parts of the body. Angiogenesis inhibition therefore benefits cancer patients. Angiogenesis also is required at times such as wound healing. These wounds can be external wounds or internal organ wounds that result from accidents, burns, injury and surgery. Thus, agents that promote angiogenesis have a great potential for use in therapy for wound healing.

The application of the compounds of the invention for modulation of cholesterol metabolism is also contemplated. For example, certain saponins are known to have the effect of lowering the serum cholesterol levels of human patients. Therefore, by treating patients with the triterpene saponins identified herein, either orally or intravenously, the morbidity associated with high cholesterol and related cardiovascular diseases may be decreased. Further, for the treatment of cardiovascular conditions, it is contemplated that the compounds of the invention may be used for the treatment of arrhythmic action and further may be used as a vascular relaxant, resulting in an antihypertensive activity.

Another potential application of the compounds of the invention is as an anti-inflammatory agent. Significantly, recent evidence suggests the involvement of the inflammatory response in carcinogenesis. Treatment of patients with the compounds of the invention may, therefore, potentially alleviate a wide degree of ailments associated with inflammation, including tumorigenesis and tissue damage. Such stages of inflammation that may be affected include increased blood vessel permeability and release (exudation) of histamine, serotonin and basic polypeptides and proteins, accompanied by hyperaemia and oedema formation, as well as cellular infiltration and formation of new conjunctive tissue.

Further use may be found as ingredients in topical agents, for example, as agents for protection from skin aging and/or carcinogenesis, whether due to endogenous or external factors. For example, a suitable application comprises the use of the compounds of the invention as an ingredient in sunblock, or other similar lotions for application to human skin. The potential benefit of such a composition is indicated by the anti-tumor activities identified herein for certain of the compounds of the invention. Such lotions and sunblocks containing the compounds of the invention may, therefore, be particularly suited to those with a predisposition to various forms of skin damage or cancer, including the fair skinned or those with a genetic predisposition to skin cancer.

Other possible applications of the compounds include use as an antioxidant, for modulating production of nitrous oxide in cells, for protection of the central nervous system from damage, and for the treatment of hypertension or atherosclerosis. In addition, the inventors specifically envision the topical application of the compounds of the invention for enhanced penile function.

II. Inhibition of Tumor Cell Growth with the Compounds of the Invention

Many types of cell lines have been used to display the growth inhibitory properties of soybean isoflavonoids and soy saponins. These have included human cancer cell lines from prostate (LNCaP, DU 145, PC-3), breast carcinoma (MDA-468, MCF-7, MCF-7-D-40, MDA-MB-231), stomach (HSC-41E6, HSC-45M2, SH101-P4), colon (HT29 clone 19A), bladder (HT-1376, UM-UC-3, RT-4, J82, TCCSUP), melanoma (B16F-10), leukemia (HL-60) and carcinoma (HCT-15) and rat prostate (MAT-LyLu).

Here, as described herein below, the inventors used human stomach carcinoma (Hs 740.T, Hs 756 T), breast adenocarcinoma (Hs 578 T, Hs 742.T) and prostate carcinoma (DU 145, and LNCaP-FGC) cell lines to evaluate the cytotoxic activities of extracts and the compounds provided the invention. The 50% effective doses (ED50) obtained by measuring growth inhibition with MTT (3-[4,5-dimethlthiazol-2-yl]-2,5-diphenyltetrazolium bromide]) (Goren et al, 1996; Rubinstein et al, 1990) are shown in Table 3. As can be seen, the results indicate that the new compounds identified exhibited cytoxic activity against tumor cells.

One aspect of the invention thus comprises use of the isolfavonoid and triterpene saponin compounds provided by the invention for the inhibition of tumor cell growth, for example, for the treatment of cancer. In the development of cancer, mammalian cells go through a series of genetically determined changes that lead to abnormal proliferation. This can occur in steps, generally referred to as (1) initiation: when an external or internal agent or stimulus triggers a genetic change in one or more cells and (2) promotion: involving further genetic and metabolic changes, which can include inflammation. During the "promotion stage," cells begin a metabolic transition to a stage of cellular growth in which apoptosis is blocked.

Cancer cells are characterized by a loss of apoptotic control in addition to a loss of control of the regulatory steps of the cell cycle. Cancer cells (malignant cells) escape normal growth control mechanisms through a series of metabolic changes during the initiation and promotion stages at the onset of malignancy. These changes are a consequence of genetic alterations in the cells. These genetic alterations may include (i) activating mutations and/or increased expression of protooncogenes and/or (ii) inactivating mutations and/or decreased expression of one or more tumor suppressor genes. Most oncogene and tumor suppressor gene products are components of signal transduction pathways that control cell cycle entry or exit, promote differentiation, sense DNA damage and initiate repair mechanisms, and/or regulate cell death programs. Nearly all tumors have mutations in multiple oncogenes and tumor suppressor genes. One can conclude that cells employ multiple parallel mechanisms to regulate cell growth, differentiation, DNA damage control, and apoptosis.

In certain aspects of the invention, the compounds described herein may be administered to a subject in need thereof to treat the subject either prophylactically to prevent a hyperproliferative disorder, including cancer, or therapeutically after the detection of the disorder. To inhibit the initiation and promotion of cancer, to kill cancer/malignant cells, to inhibit cell growth, to induce apoptosis, to inhibit metastasis, to decrease tumor size and to otherwise reverse or reduce the malignant phenotype of tumor cells, using the methods and compositions of the present invention, one would generally contact a "target" cell with the compounds described herein. This may be achieved by contacting a tumor or tumor cell with a single composition or pharmacological formulation that includes the compounds of the invention, or by contacting a tumor or tumor cell with more than one distinct composition or formulation, at the same time, wherein one composition includes a compound of the invention and the other includes a second agent.

Preferred cancer cells for treatment with the instant invention include, for example, epithelial cancers such as skin, colon, uterine, ovarian, pancreatic, lung, bladder, breast, renal and prostate tumor cells. Other target cancer cells include cancers of the brain, liver, stomach, esophagus, head and neck, testicles, cervix, lymphatic system, larynx, esophagus, parotid, biliary tract, rectum, uterus, endometrium, kidney, bladder, and thyroid; including squamous cell carcinomas, adenocarcinomas, small cell carcinomas, gliomas, neuroblastomas, and the like. However, this list is for illustrative purposes only, and is not limiting, as potentially any tumor cell could be treated with the compounds of the instant invention. Assay methods for ascertaining the relative efficacy of the compounds of the invention in treating the above types of tumor cells and other tumor cells are specifically disclosed herein and will be apparent to those of skill in the art in light of the present disclosure.

The compounds of the present invention are preferably administered as a pharmaceutical composition comprising a pharmaceutically or pharmacologically acceptable diluent or carrier. The nature of the carrier is dependent on the chemical properties of the compound(s) employed, including solubility properties, and/or the mode of administration. For example, if oral administration is desired, a solid carrier may be selected, and for i.v. administration a liquid salt solution carrier may be used.

The phrases "pharmaceutically or pharmacologically acceptable" refer to molecular entities and compositions that do not produce an adverse, allergic or other untoward reaction when administered to an animal, or a human, as appropriate. As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

(i) Treatment Protocol

Two approaches are envisioned for illustrative purposes for the use of the compounds of the invention either alone or in combination therapy. The first is the use in metastatic cancer either in patients who have not received prior chemo, radio, or biological therapy or in previously untreated patients. Patients would be treated by systemic administration, that is, intravenous, subcutaneous, oral administration or by intratumoral injection. The pharmaceutical dose(s) administered would preferably contain between 10 and 25 mg of the compounds of the invention, for example the compounds of formulas I–VI, per kg of patient body weight per day, including about 13, 16, 19, and 22 mg/kg/day. Alternatively, the patient could be treated with one or more pharmaceutical compositions comprising from about 1 mg/kg/day of the compounds of the invention to about 100 mg/kg/day, including about 3, 6, 9, 12, 15, 18, 21, 28, 30, 40, 50, 60, 70, 80 and 90 mg/kg/day of the compounds.

The treatment course typically consists of daily treatment for a minimum of eight weeks or one injection weekly for a minimum of eight weeks. Upon election by the clinician, the regimen may be continued on the same schedule until the tumor progresses or the lack of response is observed.

Another application of the compounds of the invention is in treating patients who have been rendered free of clinical disease by surgery, chemotherapy, and/or radiotherapy. Adjuvant therapy would be administered in the same regimen as described above for a minimum of one year to prevent recurrent disease.

(ii) Prevention of Cancer with the Compounds of the Invention

Another application of the compounds and mixtures of the invention is in the prevention of cancer in high risk groups. Such patients (for example, those with genetically defined predisposition to tumors such as breast cancer, colon cancer, skin cancer, and others) would be treated by mouth (gastrointestinal tumors), topically on the skin (cutaneous), or by systemic administration for a minimum period of one year and perhaps longer to determine prevention of cancer. This use would include patients and well defined pre-neoplastic lesions, such as colorectal polyps or other premalignant lesions of the skin, breast, lung, or other organs.

(iii) Clinical Protocol

A clinical protocol has been designed by the inventors to facilitate the treatment of cancer using the compounds of the invention. In accordance with this protocol, patients having histologic proof of cancer, for example, ovarian cancer, pancreatic cancer, renal cancer, prostate cancer, lung, or bladder will be selected. Patients may, but need not have received previous chemo-, radio- or gene therapies. Optimally, patients will have adequate bone marrow function (defined as peripheral absolute granulocyte count of >2,000/mm$^3$ and platelet count of 100,000/mm$^3$), adequate liver function (bilirubin $\leq$1.5 mg/dl) and adequate renal function (creatinine <1.5 mg/dl).

The protocol calls for single dose administration, via intratumoral injection, of a pharmaceutical composition containing about 10 to 25 mg of the compounds of the invention per kg of patient body weight. For tumors of $\geq$4 cm, the volume administered will be 4–10 ml (preferably 10 ml), while for tumors <4 cm, a volume of 1–3 ml will be used (preferably 3 ml). Multiple injections will be delivered for a single dose, in 0.1–0.5 ml volumes, with spacing of approximately 1 cm or more.

The treatment course consists of about six doses, delivered over two weeks. Upon election by the clinician, the regimen may be continued, six doses each two weeks, or on a less frequent (monthly, bimonthly, quarterly, etc.) basis.

Where patients are eligible for surgical resection, the tumor will be treated as described above for at least two consecutive two-week treatment courses. Within one week of completion of the second (or more, e.g., third, fourth, fifth, sixth, seventh, eighth, etc.) course, the patient will receive surgical resection. Prior to close of the incision, 10 ml of a pharmaceutical composition containing the compounds of the invention will be delivered to the surgical site (operative bed) and allowed to remain in contact for at least 60 minutes. The wound is closed and a drain or catheter placed therein. On the third post-operative day, an additional 10 ml of the pharmaceutical composition is administered via the drain and allowed to remain in contact with the operative bed for at least two hours. Removal by suction is then performed, and the drain removed at a clinically appropriate time.

(iv) Treatment of Artificial and Natural Body Cavities

One of the prime sources of recurrent cancer is the residual, microscopic disease that remains at the primary tumor site, as well as locally and regionally, following tumor excision. In addition, there are analogous situations where natural body cavities are seeded by microscopic tumor cells. The effective treatment of such microscopic disease would present a significant advance in therapeutic regimens.

Thus, in certain embodiments, a cancer may be removed by surgical excision, creating a "cavity." Both at the time of surgery, and thereafter (periodically or continuously), the therapeutic composition of the present invention is administered to the body cavity. This is, in essence, a "topical" treatment of the surface of the cavity. The volume of the composition should be sufficient to ensure that the entire surface of the cavity is contacted by the expression construct.

In one embodiment, administration simply will entail injection of the therapeutic composition into the cavity formed by the tumor excision. In another embodiment, mechanical application via a sponge, swab or other device may be desired. Either of these approaches can be used subsequent to the tumor removal as well as during the initial surgery. In still another embodiment, a catheter is inserted into the cavity prior to closure of the surgical entry site. The cavity may then be continuously perfused for a desired period of time.

In another form of this treatment, the "topical" application of the therapeutic composition is targeted at a natural body cavity such as the mouth, pharynx, esophagus, larynx, trachea, pleural cavity, peritoneal cavity, or hollow organ cavities including the bladder, colon or other visceral organs. In this situation, there may or may not be a significant, primary tumor in the cavity. The treatment targets microscopic disease in the cavity, but incidentally may also affect a primary tumor mass if it has not been previously removed or a pre-neoplastic lesion which may be present within this cavity. Again, a variety of methods may be employed to affect the "topical" application into these visceral organs or cavity surfaces. For example, the oral cavity in the pharynx may be affected by simply oral swishing and gargling with solutions. However, topical treatment within the larynx and trachea may require endoscopic visualization and topical delivery of the therapeutic composition. Visceral organs such as the bladder or colonic mucosa may require indwelling catheters with infusion or again direct visualization with a cystoscope or other endoscopic instrument. Cavities such as the pleural and peritoneal cavities may be accessed by indwelling catheters or surgical approaches which provide access to those areas.

(v) Chemotherapeutic Combinations and Treatment

In certain embodiments of the present invention, it may be desirable to administer the compounds of the invention in combination with one or more other agents having anti-tumor activity including chemotherapeutics, radiation, and therapeutic proteins or genes. This may enhance the overall anti-tumor activity achieved by therapy with the compounds of the invention alone, or may be used to prevent or combat multi-drug tumor resistance.

To use the present invention in combination with the administration of a second chemotherapeutic agent, one would simply administer to an animal a compound of the invention in combination with the second therapeutic agent in a manner effective to result in their combined anti-tumor actions within the animal. These agents would, therefore, be provided in an amount effective and for a period of time effective to result in their combined presence within the tumor vasculature and their combined actions in the tumor environment. To achieve this goal, the agents may be administered to the animal simultaneously, either in a single composition or as two distinct compositions using different administration routes.

Alternatively, the compounds of the invention may precede or follow the chemotherapeutic agent, radiation or protein or gene therapy treatment by intervals ranging from minutes to weeks. In embodiments where the second agent and the compounds of the invention are administered separately to the animal, one would generally ensure that a significant period of time did not expire between the time of each delivery, such that the additional agent and the compound of the invention would still be able to exert an advantageously combined effect on the tumor. In such instances, it is contemplated that one would contact the tumor with both agents within about 5 minutes to about one week of each other and, more preferably, within about 12–72 hours of each other, with a delay time of only about 24–48 hours being most preferred. In some situations, it may be desirable to extend the time period for treatment significantly, where several days (2, 3, 4, 5, 6 or 7) or even several weeks (1, 2, 3, 4, 5, 6, 7 or 8) lapse between the respective administrations. It also is conceivable that more than one administration of either agent will be desired. To achieve tumor regression, both agents are delivered in a combined amount effective to inhibit its growth, irrespective of the times for administration.

A variety of agents are suitable for use in the combined treatment methods disclosed herein. Chemotherapeutic agents contemplated as exemplary include, e.g., etoposide (VP-16), adriamycin, 5-fluorouracil (5-FU), camptothecin, actinomycin-D, mitomycin C, and cisplatin (CDDP).

As will be understood by those of ordinary skill in the art, the appropriate doses of chemotherapeutic agents will generally approximate those already employed in clinical therapies wherein the chemotherapeutics are administered alone or in combination with other chemotherapeutics. By way of example only, agents such as cisplatin, and other DNA alkylating agents may be used. Cisplatin has been widely used to treat cancer, with efficacious doses used in clinical applications of 20 mg/m$^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m$^2$ at 21 day intervals for adriamycin, to 35–50 mg/m$^2$ for etoposide intravenously or double the intravenous dose orally.

Agents that disrupt the synthesis and fidelity of polynucleotide precursors also may be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU is applicable in a wide range of carriers, including topical, with intravenous administration in doses ranging from 3 to 15 mg/kg/day being commonly used.

Exemplary chemotherapeutic agents that are useful in connection with combined therapy are listed in Table 2. Each of the agents listed therein are exemplary and by no means limiting. In this regard, the skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

TABLE 2

Chemotherapeutic Agents Useful In Neoplastic Disease

| CLASS | TYPE OF AGENT | NONPROPRIETARY NAMES (OTHER NAMES) | DISEASE |
|---|---|---|---|
| Alkylating Agents | Nitrogen Mustards | Mechlorethamine (HN$_2$) | Hodgkin's disease, non-Hodgkin's lymphomas |
| | | Cyclophosphamide Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) Chlorambucil | Multiple myeloma, breast, ovary Chronic lymphocytic leukemia, primary macroglobulinemia, Hodgkin's disease, non-Hodgkin's lymphomas |
| | Ethylenimenes and Methylmelamines | Hexamethylmelamine Thiotepa | Ovary Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |

TABLE 2-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimida-zolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU) | Breast, colon, stomach, pancreas, ovary, head and neck, urinary bladder, premalignant skin lesions (topical) |
| | | Floxuridine (fluorode-oxyuridine; FUdR) | |
| | | Cytarabine (cytosine arabinoside) | Acute granulocytic and acute lymphocytic leukemias |
| | Purine Analogs and Related Inhibitors | Mercaptopurine (6-mercaptopurine; 6-MP) | Acute lymphocytic, acute granulocytic and chronic granulocytic leukemias |
| | | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |

TABLE 2-continued

Chemotherapeutic Agents Useful In Neoplastic Disease

| CLASS | TYPE OF AGENT | NONPROPRIETARY NAMES (OTHER NAMES) | DISEASE |
|---|---|---|---|
| | Methyl Hydrazine Derivative | Procarbazine (N-methylhydrazine, MIH) | Hodgkin's disease |
| | Adrenocortical Suppressant | Mitotane (o,p'-DDD) Aminoglutethimide | Adrenal cortex Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

Other factors that cause DNA damage and have been used extensively include what are commonly known as γ-rays, X-rays, and/or the directed delivery of radioisotopes to tumor cells. Other forms of DNA damaging factors also are contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

(vi) Targeted Cancer Therapy

The compounds described herein may be linked to one or more molecules which target the compounds to tumor cells. Targeting is beneficial in that it can be used to increase the overall levels of a drug at the site of treatment, for example, at tumor sites, while minimizing systemic exposure to the drug. In common with the chemotherapeutic agents discussed above, it is possible that the use of a targeted compound may be used in combination with a second agent, such as a chemotherapeutic agent. Both the first and the second agent be directed to the same or different targets within the tumor environment. This should result in additive, greater than additive or even markedly synergistic results.

Exemplary targeting agents employed in combination with the compounds of the present invention will be those targeting agents that are capable of delivering the active molecules to the tumor region, i.e., capable of localizing within a tumor site. Similarly desired will be those agents which target the vasculature of a tumor region. The targeting of the compounds is specifically contemplated to allow for greater effective concentrations in tumor regions without or with the minimization of potential side effects which could be observed with a somewhat wider or systemic distribution of the compounds. Specifically, the targeting agent may be directed to components of tumor cells; components of tumor vasculature; components that bind to, or are generally associated with, tumor cells; components that bind to, or are generally associated with, tumor vasculature; components of the tumor extracellular matrix or stroma or those bound therein; and even cell types found within the tumor vasculature.

1. Tumor Cell Targets and Antibodies

The malignant cells that make up the tumor may be targeted using a bispecific antibody that has a region capable of binding to a relatively specific marker or antigen of the tumor cell. For example, specific tumor cell inhibition or killing may be achieved by the binding of an antibody-active molecule composition conjugate to a target tumor cell.

Many so-called "tumor antigens" have been described, any one which could be employed as a target in connection with the targeted aspects of the present invention. A large number of exemplary solid tumor-associated antigens are listed herein below. The preparation and use of antibodies against such antigens is well within the skill of the art and specifically disclosed herein. Exemplary antibodies include those from gynecological tumor sites (see, e.g., the ATCC Catalogue): OC 125; OC 133; OMI; Mo v1; Mo v2; 3C2; 4C7; ID$_3$; DU-PAN-2; F 36/22; 4F$_7$/7A$_{10}$; OV-TL3; B72.3; DF$_3$ 2C$_8$/2F$_7$; MF 116; Mov18; CEA 11-H5; CA 19-9 (1116NS 19-9); H17-E2; 791T/36; NDOG$_2$; H317; 4D5, 3H4, 7C2, 6E9, 2C4, 7F3, 2H11, 3E8, 5B8, 7D3, SB8; HMFG2; 3.14.A3; from breast tumor sites: DF3; NCRC-11; 3C6F9; MBE6; CLNH5; MAC 40/43; EMA; HMFG1 HFMG2; 3.15.C3; M3, M8, M24; M18; 67-D-11; D547Sp, D75P3, H222; Anti-EGF; LR-3; TA1; H59; 10-3D-2; HmAB,12; MBR 1,2,3; 24•17•1; 24•17•2 (3E1•2) F36/ 22.M7/105; C11, G3, H7; B6•2; B1•1; Cam 17•1; SM3; SM4; C-Mul (566); 4D5 3H4, 7C2, 6E9, 2C4, 7F3, 2H11, 3E8, 5B8, 7D3, 5B8; OC 125; MO v2; DU-PAN-2; 4F$_7$/ 7A$_{10}$; DF$_3$; B72•3; ccccCEA 11; H17-E2; 3•14•A3;

FO23C5; from colorectal tumor sites: B72•3; (17-1A) 1083-17-1A; CO17-1A; ZCE-025; AB2; HT-29-15; 250-30.6; 44X14; A7; GA73•3; 791T/36; 28A32; 28.19.8; X MMCO-791; DU-PAN-2; ID$_3$; CEA 11-H5; 2C$_8$/2F$_7$; CA-19-9 (1116NS 19-9); PR5C5; PR4D2; PR4D1; from melanoma sites 4•1; 8•2 M$_{17}$; 96•5; 118•1, 133•2, (113•2); L$_1$, L$_{10}$, R$_{10}$(R$_{19}$); I$_{12}$; K$_5$; 6•1; R24; 5•1; 255.28S; 465.12S; 9•2•27; F11; 376.96S; 465.12S; 15•75; 15•95; Mel-14; Mel-12; Me3-TB7; 225.28SD; 763.24TS; 705F6; 436910; M148; from gastrointestinal tumors: ID3; DU-PAN-2; OV-TL3; B72•3; CEA 11-H5; 3•14•A3; C COLI; CA-19-9 (1116NS 19-9) and CA50; OC125; from lung tumors: 4D5 3H4, 7C2, 6E9, 2C4, 7F3, 2H11, 3E8, 5B8, 7D3, SB8; MO v2; B72•3; DU-PAN-2; CEA 11-H5; MUC 8-22; MUC 2-63; MUC 2-39; MUC 7-39; and from miscellaneous tumors: PAb 240; PAb 246; PAb 1801; ERIC•1; M148; FMH25; 6•1; CA1; 3F8; 4F$_7$/7A$_{10}$; 2C$_8$/2F$_7$; CEA 11-H5.

Another means of defining and targeting a tumor is in terms of the characteristics of a tumor cell itself, rather than describing the biochemical properties of an antigen expressed by the cell. A number of exemplary tumor cell lines are known and may be used for the preparation of targeting agents. For example, whole cells or cell homogenates from known tumor lines could be used to prepare anti-tumor antibodies for the targeting of related tumors types. Similarly, such tumor cell lines may find use in the implementation of various in vitro assays. In this regard, the skilled artisan is referred to the ATCC catalogue for the purpose of exemplifying human tumor cell lines that are publicly available (from ATCC Catalogue). Exemplary cell lines include J82; RT4; ScaBER; T24; TCCSUP; 5637; SK-N-MC; SK-N-SH; SW 1088; SW 1783; U-87 MG; U-118 MG; U-138 MG; U-373 MG; Y79; BT-20; BT-474; MCF7; MDA-MB-134-VI; MDA-MD-157; MDA-MB-175-VII; MDA-MB-361; SK-BR-3; C-33 A; HT-3; ME-180; MS751; SiHa; JEG-3; Caco-2; HT-29; SK-CO-1; HuTu 80; A-253; FaDu; A-498; A-704; Caki-1; Caki-2; SK-NEP-1; SW 839; SK-HEP-1; A-427; Calu-1; Calu-3; Calu-6; SK-LU-1; SK-MES-1; SW 900; EB1; EB2; P3HR-1; HT-144; Malme-3M; RPMI-7951; SK-MEL-1; SK-MEL-2; SK-MEL-3; SK-MEL-5; SK-MEL-24; SK-MEL-28; SK-MEL-31; Caov-3; Caov-4; SK-OV-3; SW 626; Capan-1; Capan-2; DU 145; A-204; Saos-2; SK-ES-1; SK-LMS-1; SW 684; SW 872; SW 982; SW 1353; U-2 OS; Malme-3; KATO III; Cate-1B; Tera-1; Tera-2; SW579; AN3 CA; HEC-1-A; HEC-1-B; SK-UT-1; SK-UT-1B; SW 954; SW 962; NCI-H69; NCI-H128; BT-483; BT-549; DU4475; HBL-100; Hs 578Bst; Hs 578T; MDA-MB-330; MDA-MB-415; MDA-MB-435S; MDA-MB-436; MDA-MB-453; MDA-MB-468; T-47D; Hs 766T; Hs 746T; Hs 695T; Hs 683; Hs 294T; Hs 602; JAR; Hs 445; Hs 700T; H4; Hs 696; Hs 913T; Hs 729; FHs 738Lu; FHs 173We; FHs 738Bl; NIH:OVCAR-3; Hs 67; RD-ES; ChaGo K-1; WERI-Rb-1; NCI-H446; NCI-H209; NCI-H146; NCI-H441; NCI-H82; H9; NCI-H460; NCI-H596; NCI-H676B; NCI-H345; NCI-H820; NCI-H520; NCI-H661; NCI-H510A; D283 Med; Daoy; D341 Med; AML-193 and MV4-11.

One may consult the ATCC Catalogue of any subsequent year to identify other appropriate cell lines. Also, if a particular cell type is desired, the means for obtaining such cells, and/or their instantly available source, will be known to those of skill in the particular art. An analysis of the scientific literature will thus readily reveal an appropriate choice of cell for any tumor cell type desired to be targeted.

As explained above, antibodies constitute a straightforward means of recognizing a tumor antigen target. An extensive number of antibodies are known that are directed against solid tumor antigens. Certain useful anti-tumor antibodies are listed above. However, as will be known to those of skill in the art, certain of the antibodies listed will not have the appropriate biochemical properties, or may not be of sufficient tumor specificity, to be of use therapeutically. An example is MUC8-22 that recognizes a cytoplasmic antigen. Antibodies such as these will generally be of use only in investigational embodiments, such as in model systems or screening assays.

Generally speaking, antibodies for use in these aspects of the present invention will preferably recognize antigens that are accessible on the cell-surface and that are preferentially, or specifically, expressed by tumor cells. Such antibodies will also preferably exhibit properties of high affinity, such as exhibiting a $K_d$ of <200 nM, and preferably, of <100 nM, and will not show significant reactivity with life-sustaining normal tissues, such as one or more tissues selected from heart, kidney, brain, liver, bone marrow, colon, breast, prostate, thyroid, gall bladder, lung, adrenals, muscle, nerve fibers, pancreas, skin, or other life-sustaining organ or tissue in the human body. The "life-sustaining" tissues that are the most important for the purposes of the present invention, from the standpoint of low reactivity, include heart, kidney, central and peripheral nervous system tissues and liver. The term "significant reactivity," as used herein, refers to an antibody or antibody fragment that, when applied to the particular tissue under conditions suitable for immunohistochemistry, will elicit either no staining or negligible staining with only a few positive cells scattered among a field of mostly negative cells.

Particularly promising antibodies are those having high selectivity for a solid tumor. For example, antibodies binding to TAG 72 and the HER-2 proto-oncogene protein, which are selectively found on the surfaces of many breast, lung and colorectal cancers (Thor et al., 1986; Colcher et al., 1987; Shepard et al., 1991); MOv18 and OV-TL3 and antibodies that bind to the milk mucin core protein and human milk fat globule (Miotti et al., 1985; Burchell et al., 1983); and the antibody 9.2.27 that binds to the high M$_r$ melanoma antigens (Reisfeld et al., 1982). Further useful antibodies are those against the folate-binding protein, which is known to be homogeneously expressed in almost all ovarian carcinomas; those against the erb family of oncogenes that are over-expressed in squamous cell carcinomas and the majority of gliomas; and other antibodies known to be the subject of ongoing pre-clinical and clinical evaluation.

The antibodies B3, KSI/4, CC49, 260F9, XMMCO-791, D612 and SM3 are believed to be particularly suitable for use in clinical embodiments, following the standard pre-clinical testing routinely practiced in the art. B3 (U.S. Pat. No. 5,242,813; Brinkmann et al., 1991) has ATCC Accession Number HB 10573; KS1/4 can be made as described in U.S. Pat. No. 4,975,369; and D612 (U.S. Pat. No. 5,183,756) has ATCC Accession Number HB 9796.

Another means of defining a tumor-associated target is in terms of the characteristics of the tumor cell, rather than describing the biochemical properties of an antigen expressed by the cell. Accordingly, the inventors contemplate that any antibody that preferentially binds to a tumor cell may be used as the targeting component of a conjugate. The preferential tumor cell binding is again based upon the antibody exhibiting high affinity for the tumor cell and not having significant reactivity with life-sustaining normal cells or tissues, as defined above.

The invention also provides several means for generating an antibody for use in the targeting of tumor cells as described herein. To generate a tumor cell-specific antibody, one would immunize an animal with a composition comprising a tumor cell antigen and, as described more fully below, select a resultant antibody with appropriate specificity. The immunizing composition may contain a purified, or partially purified, preparation of any of the antigens listed above; a composition, such as a membrane preparation, enriched for any of the antigens in listed above; any of the cells listed above; or a mixture or population of cells that include any of the cell types listed above.

Of course, regardless of the source of the antibody, in the practice of the invention in human treatment, one will prefer to ensure in advance that the clinically-targeted tumor expresses the antigen ultimately selected. This is achieved by means of a fairly straightforward assay involving antigenically testing a tumor tissue sample, for example, a surgical biopsy, or perhaps testing for circulating shed antigen. This can readily be carried out in an immunological screening assay such as an ELISA (enzyme-linked immunosorbent assay), wherein the binding affinity of antibodies from a "bank" of hybridomas are tested for reactivity against the tumor. Antibodies demonstrating appropriate tumor selectivity and affinity are then selected for the preparation of bispecific antibodies of the present invention.

Due to the well-known phenomenon of cross-reactivity, it is contemplated that useful antibodies may result from immunization protocols in which the antigens originally employed were derived from an animal, such as a mouse or a primate, in addition to those in which the original antigens were obtained from a human cell. Where antigens of human origin are used, they may be obtained from a human tumor cell line, or may be prepared by obtaining a biological sample from a particular patient in question. Indeed, methods for the development of antibodies that are "custom-tailored" to the patient's tumor are known (Stevenson et al., 1990) and are contemplated for use in connection with this invention.

2. Methods for Antibody Production

As indicated, antibodies may find use in certain embodiments of the instant invention. For example, antibodies may be produced which are specific for a particular region in a patient or a particular tissue type. These antibodies may then be conjugated to a compound of the invention, thereby allowing the specific targeting of the compounds to the tissue for which the antibody is directed to. An exemplary embodiment of such an antibody is one which binds to a tumor cell. In a preferred embodiment of the invention, an antibody is a monoclonal antibody. Means for preparing and characterizing monoclonal and polyclonal antibodies are well known in the art and specifically disclosed herein below (see, e.g., Harlow and Lane, 1988).

Briefly, a polyclonal antibody is prepared by immunizing an animal with an immunogen comprising the desired target antigen and collecting antisera from that immunized animal. A wide range of animal species can be used for the production of antisera. Typically an animal used for production of anti-antisera is a non-human animal including rabbits, mice, rats, hamsters, pigs or horses. Because of the relatively large blood volume of rabbits, a rabbit is a preferred choice for production of polyclonal antibodies.

Antibodies, both polyclonal and monoclonal, specific for isoforms of antigen may be prepared using conventional immunization techniques, as will be generally known to those of skill in the art. A composition containing antigenic epitopes of particular cell types or, alternatively, the compounds of the present invention, can be used to immunize one or more experimental animals, such as a rabbit or mouse, which will then proceed to produce specific antibodies against the antigens. Polyclonal antisera may be obtained, after allowing time for antibody generation, simply by bleeding the animal and preparing serum samples from the whole blood.

An exemplary embodiment of the use of antibodies with the invention comprises preparing antibodies directed to tumor-specific antigens, linking the antibodies to the compounds of the invention, and treating human patients with the antigen conjugate, whereby the compounds of the invention are specifically targeted to tumor cells or other cells which are involved in a condition which can be treated with the compounds of the invention. In general, both polyclonal and monoclonal antibodies against various antigens may be employed in different embodiments of the invention. For example, they may be employed in purifying compounds in an antibody affinity column. Means for preparing and characterizing such antibodies are well known in the art and are disclosed in, for example, Harlow and Lane, 1988, the disclosure of which is specifically incorporated herein by reference in its entirety.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin also can be used as carriers. Means for conjugating a polypeptide to a carrier protein are well known in the art and include glutaraldehyde, m-maleimido-bencoyl-N-hydroxysuccinimide ester, carbodiimide and bis-biazotized benzidine.

As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

MAbs may be readily prepared through use of well-known techniques, such as those exemplified in U.S. Pat. No. 4,196,265, the disclosure of which is specifically incorporated herein by reference in its entirety. Typically, this technique involves immunizing a suitable animal with a selected immunogen composition, for example, a purified or partially purified tumor-specific antigen, polypeptide or peptide or tumor cell. The immunizing composition is administered in a manner effective to stimulate antibody producing cells. Rodents such as mice and rats are preferred animals, however, the use of rabbit, sheep or frog cells also is possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency and enzyme deficiencies that render them incapable of growing in certain selective media which support the growth of only the desired fused cells (hybridomas).

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al., (1977). The use of electrically induced fusion methods also is appropriate (Goding, 1986).

Fusion procedures usually produce viable hybrids at low frequencies, around $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (BPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

3. Further Tumor Cell Targets and Binding Ligands

In addition to the use of antibodies, other ligands could be employed to direct a compound of the invention to a tumor site by binding to a tumor cell antigen. For tumor antigens that are over-expressed receptors (e.g., an estrogen receptor, EGF receptor), or mutant receptors, the corresponding ligands could be used as targeting agents.

In an analogous manner to endothelial cell receptor ligands, there may be components that are specifically, or preferentially, bound to tumor cells. For example, if a tumor antigen is an over-expressed receptor, the tumor cell may be coated with a specific ligand in vivo. Therefore, the ligand could then be targeted either with an antibody against the ligand, or with a form of the receptor itself. Specific examples of these type of targeting agents are antibodies against TIE-1 or TIE-2 ligands, antibodies against platelet factor 4, and leukocyte adhesion binding protein.

4. Toxins

For certain applications, it is envisioned that the second therapeutic agents used in combination with the compounds described herein will be pharmacologic agents conjugated to antibodies or growth factors, particularly cytotoxic or otherwise anti-cellular agents having the ability to kill or suppress the growth or cell division of endothelial cells. In general, the invention contemplates the use of any pharmacologic agent, including and in supplement to the compounds described herein, that can be conjugated to a targeting agent, preferably an antibody, and delivered in active form to the targeted tumor cells. Exemplary anti-cellular agents include chemotherapeutic agents, radioisotopes as well as cytotoxins. In the case of chemotherapeutic agents, the inventors believe that agents such as a steroid hormone; an anti-metabolite such as cytosine arabinoside, fluorouracil, methotrexate or aminopterin; an anthracycline; mitomycin C; a vinca alkaloid; demecolcine; etoposide; mithramycin; or an anti-tumor alkylating agent such as chlorambucil or melphalan, will be particularly preferred. Other embodiments may include agents such as a cytokine, growth factor, bacterial endotoxin or the lipid A moiety of bacterial endotoxin. In any event, it is believed that agents such as these may, if desired, be successfully linked together with the compounds of the invention to targeting agents, preferably an antibody, in a manner that will allow their targeting, internalization, release or presentation to blood components at the site of the targeted cells as required using known conjugation technology (see, e.g., Ghose et al., 1983 and Ghose et al., 1987).

A variety of chemotherapeutic and other pharmacologic agents have now been successfully conjugated to antibodies and shown to function pharmacologically (see, e.g., Vaickus et al., 1991). Exemplary antineoplastic agents that have been investigated include doxorubicin, daunomycin, methotrexate, vinblastine, and various others (Dillman et al., 1988; Pieterez et al., 1988). Moreover, the attachment of other agents such as neocarzinostatin (Kimura et al., 1983), macromycin (Manabe et al., 1984), trenimon (Ghose, 1987) and α-amanitin (Davis & Preston, 1981) has been described. Specific means for preparing conjugates between the compounds of the instant invention and appropriate targeting molecules are specifically disclosed herein above.

III. Derivatives of the Compounds of the Invention

As described in detail herein, it is contemplated that certain benefits may be achieved from the manipulation of the compounds described herein to provide them with novel characteristics, a longer in viva half-life or other beneficial properties. Alternatively, such changes may have no effect on the biological activities of the compounds of the invention. Techniques for carrying out such manipulations include, but are not limited to, manipulation or modification of a triterpene saponin or isoflavone molecule, modification or removal of sugars, and conjugation to inert carriers, such as various protein or non-protein components, including immunoglobulins and Fc portions. It will be understood that longer half-life is not coextensive with the pharmaceutical compositions for use in "slow release." Slow release formulations are generally designed to give a constant drug level over an extended period. Increasing the half-life of a drug is intended to result in high plasma levels upon administration, which levels are maintained for a longer time, but which levels generally decay depending on the pharmacokinetics of the compound.

(i) Conjugates and Linked Molecules

As described above, the compounds identified herein may be linked to particular molecules in order to improve the efficacy of the compounds in treating patients for any ailment treatable with the compounds of the invention. Illustrative embodiments of such molecules include targeting agents and agents which will increase the in vivo half life of the compounds. The compounds may be linked to such secondary molecules in any operative manner that allows each region to perform its intended function without significant impairment of biological activity, for example, the anti-tumor activity of the compounds disclosed herein.

The compounds of the present invention may be directly linked to a second compound or may be linked via a linking group. By the term "linker group" is intended one or more bifunctional molecules which can be used to covalently couple the compounds to the agent and which do not interfere with the biological activity of the compounds. The linker group may be attached to any part of the compound so long as the point of attachment does not interfere with the biological activity, for example, the anti-tumor activity of a compound of the invention.

An exemplary embodiment for linking the compounds of the invention to a second agent is by the preparation of an active ester of the compounds followed by reaction of the active ester with a nucleophilic functional group on the agent to be linked. The active esters may be prepared, for example, by reaction of a carboxyl group with an alcohol in the presence of a dehydration agent such as dicyclohexylcarbodiimide (DCC), 1-(3-dimethylaminopropyl)-3-ethylcarbodiimide (EDC), and 1-(3-dimethylamino propyl)-3-ethylcarbodiimide methiodide (EDCI). The use of EDC to form conjugates is disclosed in U.S. Pat. No. 4,526,714; PCT Appl. Publ. WO91/01750, and Arnon et al., 1980, the disclosures of which are specifically incorporated herein by reference in their entirety. The agent to be linked to the compound, for example, a tumor-specific antibody, is then mixed with the activated ester in aqueous solution to give the conjugate.

Where a linker group between a compound of the invention and the agent is desired, the active ester is prepared as described above and reacted with a linker group, for example, 2-aminoethanol, an alkylene diamine, an amino acid such as glycine, or a carboxy-protected amino acid such as glycine tert-butyl ester. If the linker contains a protected carboxy group, the protecting group is removed and the active ester of the linker is prepared (as described above). The active ester is then reacted with the second molecule to give the conjugate. Alternatively, the second agent could be derivatized with succinic anhydride to give an agent-succinate conjugate which may be condensed in the presence of EDC or EDCI with a linker derivative having a free amino or hydroxyl group on the linker (see, for example, WO91/01750, the disclosure of which is specifically incorporated herein by reference in its entirety).

It also is possible to prepare a conjugate comprising a linker with a free amino group and crosslink the free amino group with a heterobifunctional cross linker such as sulfo-succinimidyl 4-(N-maleimidocyclohexane)-1-carboxylate which will react with the free sulfhydryl groups of protein antigens.

Coupling to a linker may also be carried out by reaction of an aldehyde group with an amino linker to form an intermediate imine conjugate, followed by reduction with sodium borohydride or sodium cyanoborohydride. Examples of such linkers include amino alcohols such as 2-aminoethanol and diamino compounds such as ethylenediamine, 1,2-propylenediamine, 1,5-pentanediamine, 1,6-hexanediamine, and the like. The compound may then be coupled to the linker by first forming the succinated derivative with succinic anhydride followed by condensation with the compound-linker conjugate with DCC, EDC or EDCI. Many types of linkers are known in the art and may be used in the creation of conjugates with the compounds of the invention. A list of exemplary linkers for use with the invention is given below, in Table 1.

TABLE 1

Hetero-Bifunctional Cross-Linkers

| Linker | Reactive Toward | Advantages and Applications | Spacer Arm Length\after cross-linking |
| --- | --- | --- | --- |
| SMPT | Primary amines Sulfhydryls | Greater stability | 11.2 A |
| SPDP | Primary amines Sulfhydryls | Thiolation Cleavable cross-linking | 6.8 A |
| LC-SPDP | Primary amines Sulfhydryls | Extended spacer arm | 15.6 A |
| Sulfo-LC-SPDP | Primary amines Sulhydryls | Extended spacer arm Water-soluble | 15.6 A |

TABLE 1-continued

Hetero-Bifunctional Cross-Linkers

| Linker | Reactive Toward | Advantages and Applications | Spacer Arm Length\after cross-linking |
|---|---|---|---|
| SMCC | Primary amines Sulfhydryls | Stable maleimide reactive group Enzyme-antibody conjugation Hapten-carrier protein conjugation | 11.6 A |
| Sulfo-SMCC | Primary amines Sulfhydryls | Stable maleimide reactive group Water-soluble Enzyme-antibody conjugation | 11.6 A |
| MBS | Primary amines Sulhydryls | Enzyme-antibody conjugation Hapten-carrier protein conjugation | 9.9 A |
| Sulfo-MBS | Primary amines Sulfhydryls | Water-soluble | 9.9 A |
| SIAB | Primary amines Sulfhydryls | Enzyme-antibody conjugation | 10.6 A |
| Sulfo-SIAB | Primary amines Sulhydryls | Water-soluble | 10.6 A |
| SMPB | Primary amines Sulfhydryls | Extended spacer arm Enzyme-antibody conjugation | 14.5 A |
| Sulfo-SMPB | Primary amines Sulhydryls | Extended spacer arm Water-soluble | 14.5 A |
| EDC/Sulfo-NHS | Primary amines Carboxyl groups | Hapten-Carrier conjugation | 0 |
| ABH | Carbohydrates Nonselective | Reacts with sugar groups | 11.9 A |

(ii) Rational Drug Design

The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate a three-dimensional structure for a compound of the invention or a fragment thereof. This could be accomplished by X-ray crystallography, computer modeling or by a combination of both approaches. An alternative approach, involves the random replacement of functional groups throughout the compound and the resulting effect on function determined.

It also is possible to isolate an antibody specific for a compound of the invention, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

IV. Pharmaceutical Compositions and Administration Thereof

The invention further concerns, in certain aspects, pharmaceutical compositions comprising isolated compounds from soybeans which have been structurally characterized and methods comprising the use thereof. The purification and characterization of the compounds is described in detail herein below. Bioassays performed with these compounds on cancer cell lines have demonstrated biological activity for the compounds. Pharmaceutical compositions comprising these compounds are envisioned for various uses, including, for example, as anti-inflammatory, anti-fungicidal, anti-viral, anti-mutagenic, spermicidal or contraceptive, cardiovascular and cholesterol metabolism regulatory agents and as chemotherapeutic drugs, which may be used by themselves or in combination with other forms of cancer therapy such as chemotherapy, radiation therapy, surgery, gene therapy and immunotherapy. The combination therapies are described herein in detail. One of skill in the art will determine the effective dosages for a given therapy regimen, as described herein below.

(i) Parenteral administration

One embodiment of the invention provides formulations for parenteral administration of the compounds provided by the invention, e.g., formulated for injection via the intravenous, intramuscular, sub-cutaneous or other such routes, including direct instillation into a disease site, including a tumor site. The preparation of an aqueous composition that contains a compound of the invention will be known to those of skill in the art in light of the present disclosure. Typically, such compositions can be prepared as injectables, either as liquid solutions or suspensions; solid forms suitable for using to prepare solutions or suspensions upon the addition of a liquid prior to injection also can be prepared; and the preparations also can be emulsified.

Solutions of the active compounds as free base or pharmacologically acceptable salts can be prepared in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

The compounds can be formulated into a composition in a neutral or salt form. Pharmaceutically acceptable salts include the acid addition salts (formed with the free amino groups of the protein) which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

(ii) Other modes of administration

Other modes of administration will also find use with the subject invention. For instance, the compounds of the invention may be formulated in suppositories and, in some cases, aerosol and intranasal compositions. For suppositories, the vehicle composition will include traditional binders and carriers such as polyalkylene glycols or triglycerides. Such suppositories may be formed from mixtures containing the active ingredient in the range of about 0.5% to about 10% (w/w), preferably about 1% to about 2%.

Oral compositions may be prepared in the form of solutions, suspensions, tablets, pills, capsules, sustained release formulations, or powders. These compositions can be administered, for example, by swallowing or inhaling. Where a pharmaceutical composition is to be inhaled, the composition will preferably comprise an aerosol. Exemplary procedures for the preparation of aqueous aerosols for use with the current invention may be found in U.S. Pat. No. 5,049,388, the disclosure of which is specifically incorporated herein by reference in its entirety. Preparation of dry aerosol preparations are described in, for example, U.S. Pat. No. 5,607,915, the disclosure of which is specifically incorporated herein by reference in its entirety.

Also potentially useful is the administration of the invention compounds directly in transdermal formulations with permeation enhancers such as DMSO. These compositions can similarly include any other suitable carriers, excipients or deluents. Other topical formulations can be administered to treat certain disease indications. For example, intranasal formulations may be prepared which include vehicles that neither cause irritation to the nasal mucosa nor significantly disturb ciliary function. Diluents such as water, aqueous saline or other known substances can be employed with the subject invention. The nasal formulations also may contain preservatives such as, but not limited to, chlorobutanol and benzalkonium chloride. A surfactant may be present to enhance absorption of the subject compounds by the nasal mucosa.

(iii) Formulations and Treatments

Upon formulation, solutions will be administered in a manner compatible with the dosage formulation and in such amount as is therapeutically effective. The formulation of choice can be accomplished using a variety of excipients including, for example, pharmaceutical grades of mannitol, lactose, starch, magnesium stearate, sodium saccharin cellulose, magnesium carbonate, and the like.

Typically, the compounds of the instant invention will comprise from less than 1% to about 95% of the active ingredient, preferably about 10% to about 50%. Preferably, between about 10 mg/kg patient body weight per day and about 25 mg/kg patient body weight per day will be administered to a patient. The frequency of administration will be determined by the caregiver based on patient responsiveness. Other effective dosages can be readily determined by one of ordinary skill in the art through routine trials establishing dose response curves.

Regardless of the mode of administration, suitable pharmaceutical compositions in accordance with the invention will generally include an amount of the active compound admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, which reference is specifically incorporated herein by reference in its entirety. It should be appreciated that endotoxin contamination should be kept minimally at a safe level, for example, less that 0.5 ng/mg protein. Moreover, for human administration, preparations should meet sterility, pyrogenicity, general safety and purity standards as required by FDA Office of Biological Standards.

The therapeutically effective doses are readily determinable using an animal model, as described herein. For example, for cancer treatment, experimental animals bearing solid tumors are frequently used to optimize appropriate therapeutic doses prior to translating to a clinical environment. Such models are known to be very reliable in predicting effective therapeutic strategies.

In certain embodiments, it may be desirable to provide a continuous supply of therapeutic compositions to the patient. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion of the region of interest may be preferred. This could be accomplished by catheterization, post-operatively in some cases, followed by continuous administration of the therapeutic agent. The time period for perfusion would be selected by the clinician for the particular patient and situation, but times could range from about 1–2 hours, to 2–6 hours, to about 6–10 hours, to about 10–24 hours, to about 1–2 days, to about 1–2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

(iv) Therapeutic kits

The present invention also provides therapeutic kits comprising the compounds described herein. Such kits will generally contain, in suitable container means, a pharmaceutically acceptable formulation of at least one compound of the invention. The kits also may contain other pharmaceutically acceptable formulations, such as those containing components to target the compounds to distinct regions of a patient where treatment is needed, or any one or more of a range of drugs which may work in concert with the compounds, for example, chemotherapeutic agents.

The kits may have a single container means that contains the compounds, with or without any additional components, or they may have distinct container means for each desired agent. When the components of the kit are provided in one or more liquid solutions, the liquid solution is an aqueous solution, with a sterile aqueous solution being particularly preferred. However, the components of the kit may be provided as dried powder(s). When reagents or components are provided as a dry powder, the powder can be reconstituted by the addition of a suitable solvent. It is envisioned that the solvent also may be provided in another container means. The container means of the kit will generally include at least one vial, test tube, flask, bottle, syringe or other container means, into which a compound of the invention, and any other desired agent, may be placed and, preferably, suitably aliquoted. Where additional components are included, the kit will also generally contain a second vial or other container into which these are placed, enabling the administration of separated designed doses. The kits also may comprise a second/third container means for containing a sterile, pharmaceutically acceptable buffer or other diluent.

The kits also may contain a means by which to administer the compositions to an animal or patient, e.g., one or more needles or syringes, or even an eye dropper, pipette, or other such like apparatus, from which the formulation may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

V. Assays and Methods for Screening Active Compounds

A number of assays are known to those of skill in the art and may be used to further characterize the compounds of the invention. These include assays of biological activities as well as assays of chemical properties. The results of these assays can provide important inferences as to the properties of compounds as well as their potential applications in treating human or other mammalian patients. Assays deemed to be of particular utility in this regard include in vivo and in vitro screens of biological activity and immunoassays.

(i) In Vivo Assays

The present invention encompasses the use of various animal models. Here, the identity seen between human and mouse allows examination of the function of a potential therapeutic agent, for example, a triterpene saponin or isoflavonoid of the current invention. For example, one can utilize cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

One particularly useful type of in vivo assay of anti-tumor activity comprises the use of a mouse skin model. The mouse skin model, which represents one of the best understood experimental models of multistage carcinogenesis, has permitted the resolution of three distinct stages in the development of cancer: initiation, promotion, and progression. It is now apparent that the cellular evolution to malignancy involves the sequential alteration of proto-oncogenes and/or tumor suppressor genes, whose gene products participate in critical pathways for the transduction of signals and/or regulation of gene expression. The skin tumor promotion and progression stages are characterized by selective and sustained hyperplasia, differentiation alterations, and genetic instability leading to specific expansion of the initiated cells into papillomas and carcinomas. It has been indicated that the induction of a sustained hyperplasia correlates well with the skin tumor promoting activity of various agents such as phorbol esters, several peroxides, and chrysarobin. In the mouse skin model all known carcinogens and tumor promoters have been shown to produce a sustained epidermal hyperplasia. In general, this is preceded by an inflammatory response.

Extensive data has revealed a good correlation between carcinogenicity and mutagenicity. Most tumor-initiating agents either generate or are metabolically converted to electrophilic reactants, which bind covalently to cellular DNA. Some free radicals and modified DNA bases are free radicals that have been implicated in the tumor initiation and/or tumor promotion stages of carcinogenesis. For example, strong evidence has indicated that activation of the Ha-ras gene occurs early in the process of mouse skin carcinogenesis and perhaps is equivalent to an initiation event. It has been shown that the presence of an activated c-Ha-ras gene in mouse skin papillomas and carcinomas induced by 7,12-dimethylbenz[a]anthracene was associated with a high frequency of A-T transversions at codon 61. Subsequent studies demonstrated that this type of mutation was dependent upon the chemical initiator and independent of the promoter, suggesting a direct effect of the initiator on c-Ha-ras. Furthermore, infection of mouse skin by a virally activated Ha-ras gene (v-Ha-ras) can serve as the initiating even in two-stage carcinogenesis. It should be emphasized that all skin chemical carcinogens and skin tumor initiators have been shown to produce a mutation in Ha-ras oncogene. However, skin tumor promoters do not cause a mutation in Ha-ras.

(ii) Confirmatory In vivo and Clinical Studies

It will be understood by those of skill in the art that therapeutic agents or combinations of agents, should generally be tested in an in vivo setting prior to use in a human subject. Such pre-clinical testing in animals is routine in the art. To conduct such confirmatory tests, all that is required is an art-accepted animal model of the disease in question, such as an animal bearing a solid tumor. Any animal may be used in such a context, such as, e.g., a mouse, rat, guinea pig, hamster, rabbit, dog, chimpanzee, or such like. In the context of cancer treatment, for example, studies using small animals such as mice are widely accepted as being predictive of clinical efficacy in humans, and such animal models are therefore preferred in the context of the present invention as they are readily available and relatively inexpensive, at least in comparison to other experimental animals.

The manner of conducting an experimental animal test will be straightforward to those of ordinary skill in the art. All that is required to conduct such a test is to establish equivalent treatment groups, and to administer the test compounds to one group while various control studies are conducted in parallel on the equivalent animals in the remaining group or groups. One monitors the animals during the course of the study and, ultimately, one sacrifices the animals to analyze the effects of the treatment.

Anti-tumor studies, for example, can be conducted to determine the specific effects upon the tumor vasculature and the anti-tumor effects overall. As part of such studies, the specificity of the effects should also be monitored, including the general well being of the animals. In the context of the treatment of solid tumors, it is contemplated that effective amounts of the compounds of the invention will be those that generally result in at least about 10% of the cells within a tumor exhibiting cell death or apoptosis. Preferably, at least about 20%, about 30%, about 40%, or about 50%, of the cells at a particular tumor site will be killed. Most preferably, up to 100% of the cells at a tumor site will be killed.

The extent of cell death in a tumor is assessed relative to the maintenance of healthy tissues in all of the areas of the body. It will be preferable to use doses of the compounds of the invention capable of inducing at least about 60%, about 70%, about 80%, about 85%, about 90%, about 95% up to and including 100% tumor necrosis, so long as the doses used do not result in significant side effects or other untoward reactions in the animal. All such determinations can be readily made and properly assessed by those of ordinary skill in the art. For example, attendants, scientists and physicians can utilize such data from experimental animals in the optimization of appropriate doses for human treatment. In subjects with advanced disease, a certain degree of side effects can be tolerated. However, patients in the early stages of disease can be treated with more moderate doses in order to obtain a significant therapeutic effect in the absence of side effects. The effects observed in such experimental animal studies should preferably be statistically significant over the control levels and should be reproducible from study to study.

Those of ordinary skill in the art will further understand that combinations and doses of the compounds of the invention that result in tumor-specific necrosis towards the lower end of the effective ranges may nonetheless still be useful in connection with the present invention. For example, in embodiments where a continued application of the active agents is contemplated, an initial dose that results in only about 10% necrosis will nonetheless be useful, particularly as it is often observed that this initial reduction "primes" the tumor to further destructive assault upon subsequent re-application of the therapy. In any event, even if upwards of about 40% or so tumor inhibition is not ultimately achieved, it will be understood that any induction of thrombosis and necrosis is nonetheless useful in that it represents an advance over the state of the patients prior to treatments. Still further, it is contemplated that a dose of the compounds of the invention which prevents or decreases the likelihood of either metastasis or de novo carcinogenesis would also be of therapeutic benefit to a patient receiving the treatment.

As discussed above in connection with the in vitro test system, it will naturally be understood that combinations of agents intended for use together should be tested and optimized together. The compounds of the invention can be straightforwardly analyzed in combination with one or more chemotherapeutic drugs, immunotoxins, coaguligands or such like. Analysis of the combined effects of such agents would be determined and assessed according to the guidelines set forth above.

(iii) In vitro Assays

Screening of compounds in vitro for biological activity is also useful. In the context of cancer treatment, killing of tumor cells, or cytotoxicity, is generally exhibited by necrosis or apoptosis. Necrosis is a relatively common pathway triggered by external signals. During this process, the integrity of the cellular membrane and cellular compartments is lost. On the other hand, apoptosis, or programmed cell death, is a highly organized process of morphological events that is synchronized by the activation and deactivation of specific genes (Thompson et al., 1992; Wyllie, 1985).

An efficacious means for in vitro assaying of cytotoxicity comprises the systematic exposure of a panel of tumor cells to selected compounds. Such assays and tumor cell lines suitable for implementing the assays are well known to those of skill in the art. Particularly beneficial human tumor cell lines for use in in vitro assays of anti-tumor activity include the human ovarian cancer cell lines SKOV-3, HEY, OCC1, and OVCAR-3; Jurkat T-leukemic cells; the MDA-468 human breast cancer line; LNCaP human prostate cancer cells, human melanoma tumor lines A375-M and Hs294t; and human renal cancer cells 769-P, 786-0, A498. A preferred type of normal cell line for use as a control constitutes human FS or Hs27 foreskin fibroblast cells.

In vitro determinations of the efficacy of a compound in killing tumor cells may be achieved, for example, by assays of the expression and induction of various genes involved in cell-cycle arrest (p21, p27; inhibitors of cyclin dependent kinases) and apoptosis (bcl-2, bcl-$x_L$ and bax). To carry out this assay, cells are treated with the test compound, lysed, the proteins isolated, and then resolved on SDS-PAGE gels and the gel-bound proteins transferred to nitrocellulose membranes. The membranes are first probed with the primary antibodies (e.g., antibodies to p21, p27, bax, bcl-2 and bcl-$x_1$, etc.) and then detected with diluted horseradish peroxidase conjugated secondary antibodies, and the membrane exposed to ECL detection reagent followed by visualization on ECL-photographic film. Through analysis of the relative proportion of the proteins, estimates may be made regarding the percent of cells in a given stage, for example, the G0/G1 phase, S phase or G2/M phase.

Cytotoxicity of a compound to cancer cells also can be efficiently discerned in vitro using MTT or crystal violet staining. In this method, cells are plated, exposed to varying concentrations of the sample compounds, incubated, and stained with either MTT (3-(4,5-dimethylethiazol-2-yl)-2,5-diphenyle tetrazolium bromide; Sigma Chemical Co.) or crystal violet. MTT treated plates receive lysis buffer (20% sodium dodecyl sulfate in 50% DMF) and are subject to an additional incubation before taking an OD reading at 570 nm. Crystal violet plates are washed to extract dye with Sorenson's buffer (0.1 M sodium citrate (pH 4.2), 50% v/v ethanol), and read at 570–600 nm (Mujoo et al., 1996). The relative absorbance provides a measure of the resultant cytotoxicity.

(iv) Immunoassays

Immunoassays encompassed by the present invention include, but are not limited to those described in U.S. Pat. No. 4,367,110 (double monoclonal antibody sandwich assay) and U.S. Pat. No. 4,452,901 (Western blot). Other assays include immunoprecipitation of labeled ligands and immunocytochemistry, both in vitro and in vivo. Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections also is particularly useful.

In one exemplary ELISA, antibodies are immobilized onto a selected surface exhibiting protein affinity, such as a well in a polystyrene microtiter plate. Then, a test composition is added to the wells. After binding and washing to remove non-specifically bound immune complexes, the bound antigen may be detected. Detection is generally achieved by the addition of another antibody specific for the desired antigen and which is linked to a detectable label. This type of ELISA is a simple "sandwich ELISA". Detection also may be achieved by the addition of a second antibody specific for the desired antigen, followed by the addition of a third antibody that has binding affinity for the second antibody, with the third antibody being linked to a detectable label.

Variations of ELISA techniques are known to those of skill in the art. In one such variation, the samples suspected of containing the desired antigen are immobilized onto the well surface and then contacted with the prepared antibodies. After binding and appropriate washing, the bound immune complexes are detected. Where the initial antigen specific antibodies are linked to a detectable label, the immune complexes may be detected directly. Again, the immune complexes may be detected using a second antibody that has binding affinity for the first antigen specific antibody, with the second antibody being linked to a detectable label.

Competition ELISAs also are possible in which test samples compete for binding with known amounts of labeled antigens or antibodies. The amount of reactive species in the unknown sample is determined by mixing the sample with the known labeled species before or during incubation with coated wells. The presence of reactive species in the sample acts to reduce the amount of labeled species available for binding to the well and thus reduces the ultimate signal.

Irrespective of the format employed, ELISAs have certain features in common, such as coating, incubating or binding, washing to remove non-specifically bound species, and detecting the bound immune complexes. These are described as below.

Antigen or antibodies also may be linked to a solid support, such as in the form of plate, beads, dipstick, membrane or column matrix, and the sample to be analyzed applied to the immobilized antigen or antibody. In coating a plate with either antigen or antibody, one will generally incubate the wells of the plate with a solution of the antigen or antibody, either overnight or for a specified period. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein and solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of the antigen or antibody to the well, coating with a non-reactive material to reduce background, and washing to remove unbound material, the immobilizing surface is contacted with the clinical or biological sample to be tested under conditions effective to allow immune complex (antigen/antibody) formation. Detection of the immune complex then requires a labeled secondary binding ligand or antibody, or a secondary binding ligand or antibody in conjunction with a labeled tertiary antibody or third binding ligand.

"Under conditions effective to allow immune complex (antigen/antibody) formation" means that the conditions preferably include diluting the antigens and antibodies with solutions such as BSA, bovine gamma globulin (BGG) and phosphate buffered saline (PBS)/Tween. These added agents also tend to assist in the reduction of nonspecific background.

The suitable conditions also mean that the incubation is at a temperature and for a period of time sufficient to allow effective binding. Incubation steps are typically from about 1 to 2 to 4 hours, at temperatures preferably on the order of 25° to 27° C., or may be overnight at about 4° C. or so.

Following all incubation steps in an ELISA, the contacted surface is washed so as to remove non-complexed material. Washing often includes washing with a solution of PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection.

Preferably, this will be an enzyme that will generate color development upon incubating with an appropriate chromogenic substrate. Thus, for example, one will desire to contact and incubate the first or second immune complex with a urease, glucose oxidase, alkaline phosphatase or hydrogen peroxidase-conjugated antibody for a period of time and under conditions that favor the development of further immune complex formation, e.g., incubation for 2 hours at room temperature in a PBS-containing solution such as PBS-Tween.

After incubation with the labeled antibody, and subsequent to washing to remove unbound material, the amount of label is quantified, e.g., by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer. Alternatively, the label may be a chemiluminescent one. The use of such labels is described in U.S. Pat. Nos. 5,310,687, 5,238,808 and 5,221,605.

Methods for in vitro and in situ analysis are well known and involve assessing binding of antigen-specific antibodies to tissues, cells or cell extracts. These are conventional techniques well within the grasp of those skilled in the art. For example, the antibodies to tumor cell antigens may be used in conjunction with both fresh-frozen and formalin-fixed, paraffin-embedded tissue blocks prepared for study by immunohistochemistry (IHC). Each tissue block may consist of 50 mg of residual "pulverized" tumor. The method of preparing tissue blocks from these particulate specimens has been successfully used in previous IHC studies of various prognostic factors, e.g., in breast cancer, and is well known to those of skill in the art.

Briefly, frozen-sections may be prepared by rehydrating 50 ng of frozen pulverized tumor at room temperature in PBS in small plastic capsules; pelleting the particles by centrifugation; resuspending them in a viscous embedding medium (OCT); inverting the capsule and pelleting again by centrifugation; snap-freezing in −70° C. isopentane; cutting the plastic capsule and removing the frozen cylinder of tissue; securing the tissue cylinder on a cryostat microtome chuck; and cutting 25–50 serial sections containing an average of about 500 remarkably intact tumor cells.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and embedding the block in paraffin; and cutting up to 50 serial permanent sections.

Preferred assays comprise those directed to screening for biological activities including anti-tumor activity, such as described herein. As used herein, "anti-tumor activity" refers to the inhibition in tumor cells of cell-to-cell signaling, growth, metastasis, cell division, cell migration, soft agar colony formation, contact inhibition, invasiveness, angiogenesis, tumor progression or other malignant phenotype or the induction of apoptosis. Particularly contemplated are functional assays which include measures of the use of the compounds of the invention as anti-fungal and anti-viral agents, piscicides or molluscicides, contaceptives, anthelmintics, UV-protectants, expectorants, diuretics, anti-inflammatory agents, regulators of cholesterol metabolism, cardiovascular effectors, anti-ulcer agents, analgesics, sedatives, immunomodulators, antipyretics, regulators of angiogenesis, and as agents for decreasing capillary fragility. Such assays will be well known to those of skill in the art in light of the instant disclosure. As well as in vitro and in vivo direct assays for activity, these assays may include measures of inhibition of binding to a substrate, ligand, receptor or other binding partner by a compound of the invention.

VI. Definitions

A means "one or more." Thus, a moiety may refer to one, two, three, or more moieties.

Apoptosis is defined as a normal physiologic process of programmed cell death which occurs during embryonic development and during maintenance of tissue homeostasis. The process of apoptosis can be subdivided into a series of metabolic changes in apoptotic cells. Individual enzymatic steps of several regulatory or signal transduction pathways can be assayed to demonstrate that apoptosis is occurring in a cell or cell population, or that the process of cell death is disrupted in cancer cells. The apoptotic program is also observed by morphological features which include changes in the plasma membrane (such as loss of asymmetry), a condensation of the cytoplasm and nucleus, and internucleosomal cleavage of DNA. This is culminated in cell death as the cell degenerates into "apoptotic bodies".

Techniques to assay several enzymatic and signaling processes involved in apoptosis have been developed as standard protocols for multiparameter apoptosis research. One example of an early step in apoptosis, is the release of cytochrome c from mitochondria followed by the activation of the caspase-3 pathway (PharMingen, San Diego, Calif.). Induction of the caspases (a series of cytosolic proteases) is one of the most consistently observed features of apoptosis. In particular, caspase-3 plays a central role in the process. When caspases are activated, they cleave target proteins; one of the most important of these is PARP (poly-(ADP-ribose) polymerase, which is a protein located in the nucleus). Therefore, assays detecting release of cytochrome c, detecting caspase-3 activity and detecting PARP degradation are effective determinants of apoptosis.

Furthermore, agents that cause the release of cytochrome c from the mitochondria of malignant cells can be concluded to be likely therapies for restoring at least some aspects of cellular control of programmed cell death.

Another apoptotic assay is the Annexin-V detection (Bio-Whitaker, Walkerville, Md.). Normally, phosphotidylserine (PS) is localized on the inner membrane of the plasma membrane. However, during the early stages of apoptosis, externalization of PS takes place. Annexin-V is a calcium binding protein which binds to PS and can be observed with annexin-V-FITC staining by flow cytometry (Martin et al., 1995). The ability of cells treated with the compounds described in this invention, to bind annexin-V, is taken as an indication that cells were undergoing apoptosis.

Another assay is a PI-3-Kinase assay and to detect apoptotic activity in cells treated with mixtures of the anticancer compounds, such as the compounds of the invention. Phosphoinositide 3-kinase (PI3K), a cell membrane associated enzyme, is capable of phosphorylating the 3-position of the inositol ring of phosphatidylinositol, thus defining a new lipid signaling pathway in those cells where PI3K is active. When PI3K is active, a kinase called AKT is recruited to the cell membrane. AKT is the product of an oncogene which is catalytically activated after recruitment to the membrane. Fully activated AKT plays a crucial role in cell survival. The PI3K/AKT pathway provides a mechanism by which cells evade apoptosis. Thus, a means to inhibit PI3K in malignant cells, is a likely therapy for restoring at least some aspects of the cellular control of apoptosis.

Abnormal Proliferation is defined as a series of genetically determined changes that occur in mammalian cells in the pathological state known as cancer. This process eventually results in the loss of control of apoptosis in cancer cells. This can occur in steps, generally referred to as 1. initiation, which is defined as the stage when an external agent or stimulus triggers a genetic change in one or more cells, and 2. promotion, which is defined as the stage involving further genetic and metabolic changes, which can include inflammation. During the "promotion stage", cells begin a metabolic transition to a stage of cellular growth in which apoptosis is blocked.

Compounds of the invention refers to the novel isolfavonoid and saponin compounds identified herein, specifically including, without limitation, the compounds of Formulas I–VI and any and all possible combinations or derivatives thereof as is described herein.

Cytotoxic is defined as cell death while the term "cytostatic" is defined as an inhibition of growth and/or proliferation of cells.

Malignant cells are defined as cancer cells that escape normal growth control mechanisms through a series of metabolic changes during the initiation and promotion stages of the onset of malignancy. These changes are a consequence of genetic alterations in the cells (either activating mutations and/or increased expression of protooncogenes—and/or inactivating mutations and/or decreased expression of one or more tumor suppressor genes). Most oncogene and tumor suppressor gene products are components of signal transduction pathways that control cell cycle entry or exit, promote differentiation, sense DNA damage and initiate repair mechanisms, and/or regulate cell death programs. Cells employ multiple parallel mechanisms to regulate cell growth, differentiation, DNA damage control, and apoptosis. Nearly all tumor and malignant cells have mutations in multiple oncogenes and tumor suppressor genes.

VII. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Plant Material

Soy phytochemical concentrate (SPC) was provided as a free flowing powder by Archer Daniels Midland, Inc., Decatur, Ill. SPC was prepared as described below (Zhou et al., 1999). As described by Zhou et al., soybeans (*Glycine max* cultivated) (Zhou et al., 1999; Nwokolo and Smartt, 1996) were cracked, dehulled and flaked by standard procedures followed by hexane extraction to remove the majority of lipid. The resulting defatted soy flour was extracted with aqueous ethanol (60% v/v) to produce a mixture containing carbohydrates (0.6–0.7 g/g), isoflavonoids (0.02 g/g), fat 0.12 g/g), ash (0.04 g/g) and protein (0.05 g/g) (Zhou et al., 1999). A proprietary solid phase, hydrophobic extraction procedure was accomplished by passing the aqueous alcoholic extract over Amberlite XAD. After washing the column with water to remove carbohydrates and other water-soluble materials, the hydrophobic column was eluted with 95% ethanol, and the eluant was spray-dried to form a powder called SPC.

HPLC Analysis of the SPC powder was accomplished as follows. A sample of 1 g SPC was defatted by extraction twice with 10 mL volumes of hexane. After centrifugation, the pellet was extracted three times with 10 mL of MeOH. The MeOH extracts were combined and concentrated to give 238 mg of crude extract. A 1 mg/mL solution of the crude extract in MeOH was analyzed by HPLC. Standard curves were prepared from each of the available isoflavones.

Example 2

Chemical Analysis of Plant Extracts

To isolate compounds for spectral and chemical characterization, SPC was first suspended in water, and the water-soluble fraction was concentrated and partitioned separately into n-hexane, EtOAc and n-BuOH. Chromatographic resolution of the EtOAc-soluble fraction furnished 12 isoflavonoids (designated 1–12), three of which (designated 1–3) were new compounds. Chromatographic purification of the n-BuOH soluble fraction, furnished two new (designated 13–14) and three known soy saponins (15–17). Spectra (UV, IR, $^1$H and $^{13}$C NMR, and FABMS) for isolated isoflavones were in good agreement with reported data for daidzein (4), genistein (5), glycitein (6), biochanin A (7), daidzin (8), genistin (9), glycitin (10), daidzein-7-O-βO-D-(6"-O-acetyl-glucopyranoside) (11) and genistein-7-O-β-D-(6"-O-acetyl-glucopyranoside) (12) (Hosny and Rosazza, 1999; Chang et al., 1994; Farmakalidis and Murphy et al., 1985). Spectra (1D and 2D NMR) for saponins 15–17 confirmed their structures as soysaponin A2, or 3-O-{[β-D-galactopyranosyl-(1→2)-β-D-glucuronopyranosyl]}-22-O-[β-D-glucopyranosyl(1→3)-α-L-arabinopyranosyl]soyasapogenol A (15), soysaponin V, or 3-O-[β-D-glucopyranosyl-(1→2)-β-D-galactopyranosyl(1→2)-β-D-glucuronopyranosyl] soyasapogenol B (16), and soyasapogenol B monoglucuronide, or 3-O-[β-D-glucuronopyranosyl]soyasapogenol B (17) (Kitagawa et al., 1985; Taniyama et al., 1988; Kitagawa et al., 1984).

Figure 2:
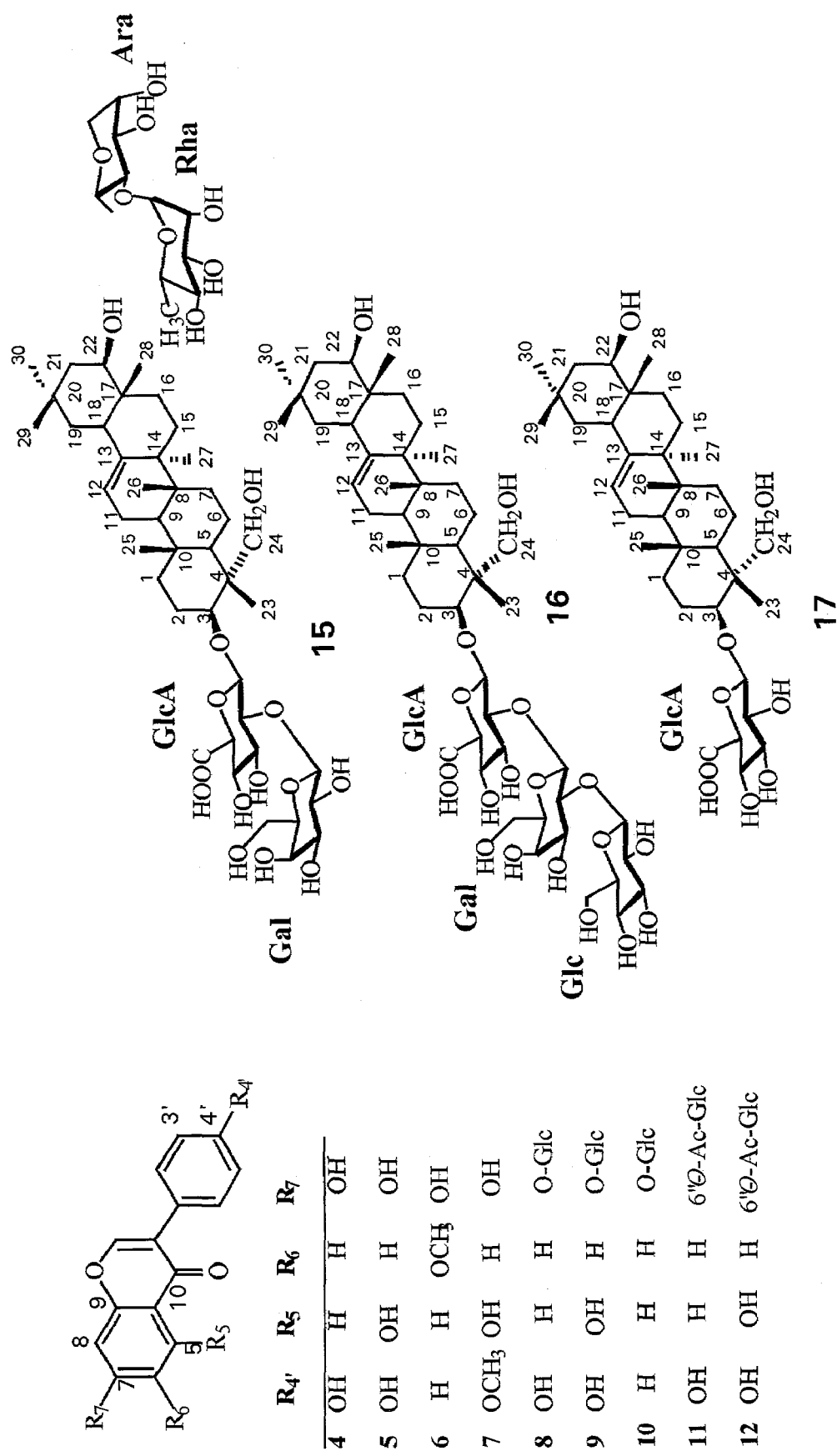
FIG. 2. Structures of known isoflavones and saponins in soybean phytochemical extract.
Figure 3:
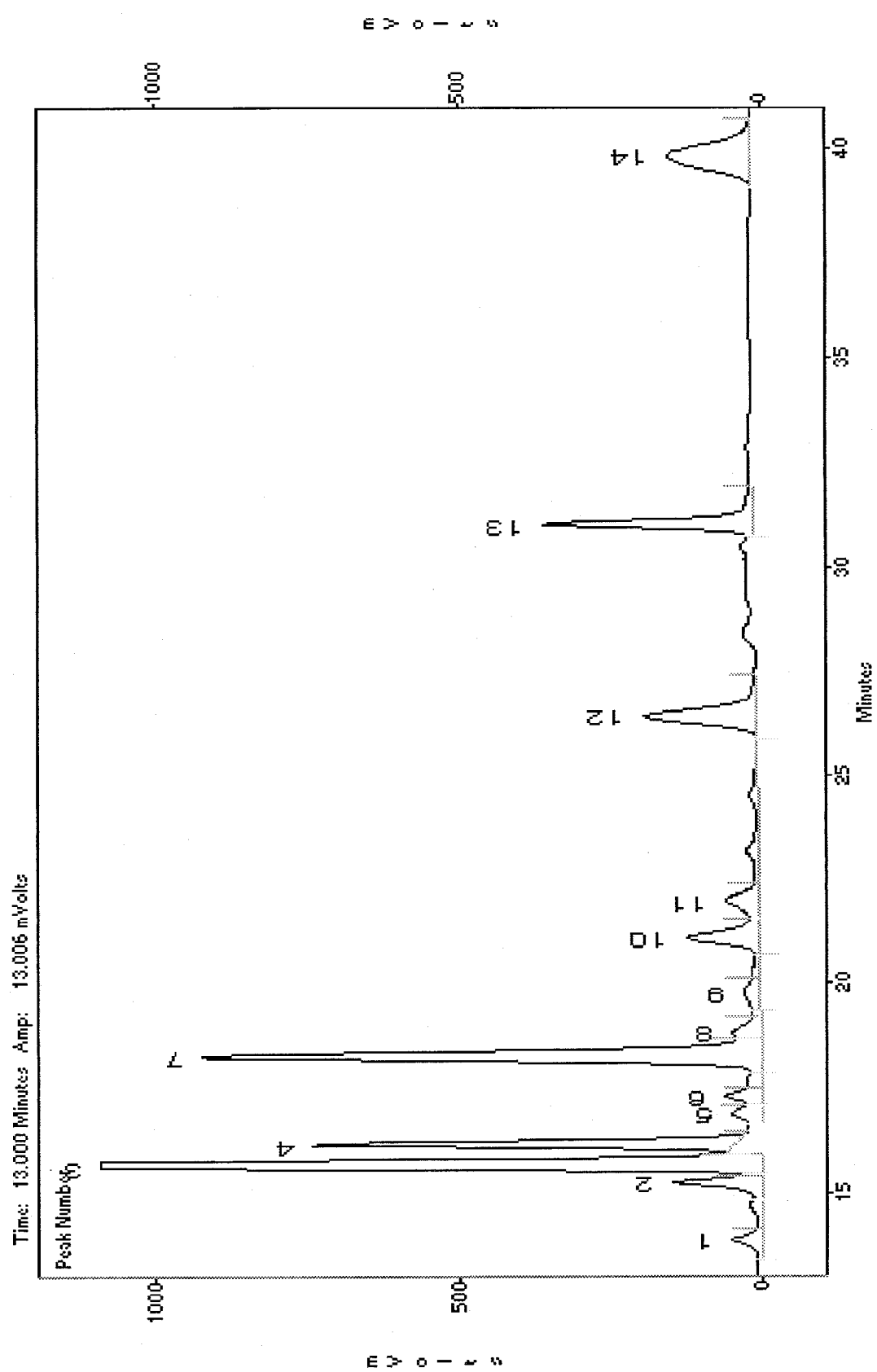
FIG. 3. HPLC analysis of soybean phytochemical methanol extract. Identified samples are peak 1, dihydrodaidzin (1), peak 2, daidzin (8), peak 3, genistin (9), peak 4, daidzein 7-O-β-D-(6"-O-acetylglucopyranoside) (11), peak 5, dihydrogenistin (2), peak 6, glycitin (10), peak 7, genistein 7-O-β-D-(6"-O-acetylglucopyranoside) (12), peak 8, unknown, peak 9, unknown, peak 10, 2", 6"-O-diacetylhlononin (3), peak 11, glycitein (6), peak 12, daidzein (4), peak 13, genistein (5), peak 14, biochanin A (7).

HPLC analysis of SPC (FIG. 3) revealed an abundance of known isoflavones together with minor eluting peaks representing unknown isoflavonoids (Hosny and Rosazza, 1999). The predominant isoflavonoids in SPC were designated 4 (1.2 mg/gm), 5 (1.6 mg/gm), 6 (0.1 mg/gm), 7 (0.2 mg/gm), 8 (0.5 mg/gm), 9 (4.3 mg/gm) 11 (3.1 mg/gm) and 12 (4.6 mg/gm) from the total extract. Concentrations of known isoflavonoids (FIG. 2) in the extract were comparable to those reported previously (Zhou et al., 1999). New compounds eluting at retention volumes of 13.89 mL, 17.34 mL and 21.14 mL were isolated and further characterized. Of the new compounds, isoflavanone 1 gave $C_{21}H_{23}O_9$ by HRFABMS. Bands for hydroxyl and chelated carbonyl functional groups were suggested by IR, and the UV absorptions at 276 and 310 nm were typical for an isoflavanone (Mabry et al., 1970). The 310 nm absorbance shifted to 318 nm after addition of NaOMe reagent indicating a free hydroxyl group at C-4', which was also evident by a m/z 120 fragment ion in the EIMS. Lack of UV bathochromic shifts with AlCl³ or NaOAc suggested the absence of free C-5 or C-7 hydroxyl groups in 1. The proton singlet typically observed between δ 8.2–8.5 for H-2 in isoflavones (4–12) was absent in 1. An AMX system with signals at δ 4.86 (1H, dd, J=4.9, 12.2 Hz, H-2a), 4.97 (1H, dd, J=7.2, 12.2 Hz, H-2b) and 3.91 (1H, t, J=4.9 Hz, H-3) indicated a flavanone structure for 1. These protons were correlated with carbon signals for C-2 and C-3 at δ 71.34 and δ 47.19 respectively, while a signal at δ 198.40 was assigned to a C-4 isoflavanone ketone (Agrawal, 1989). An ABX spin system of δ 7.38 (1H, d, J=8.6 Hz), 6.69 (1H, dd, J=2.2, 8.6 Hz) and 6.51 (1H, d, J=2.2 Hz) was attributed to H-5, H-6 and H-8, while the four-proton AA'BB' spin system was assigned to a 4'-substituted ring B.

Signals observed for five trans diaxial oxymethine protons (J=7.8 Hz) and one oxymethylene group indicated the presence of a β-D-glucopyranosyl moiety for 1. HMBC correlations confirmed assignments of C-5, C-6 and C-8. Thus, the signal for C-5 (δ 129.00) was correlated with H-6 (δ 6.69, dd, J=2.2, 8.6 Hz), while both H-6 and H-8 (δ 6.51 d J=2.2 Hz) were correlated with C-7 (δ164.60), and H-8 was correlated with C-9 (δ 155.20). The glucosyl residue was located at the 7-O-position of 1 by HMBC correlations between C-7 and the anomeric H-1". The absolute configuration at C-3 of isoflavanones remains poorly defined in the literature because of keto-enol tautomerism that compromises the isomeric composition of these compounds (Harborne et al., 1975). The optical rotation of 1 as $[\alpha]_D^{22}$ −12.9° is similar to that reported for isoflavanone sophorol ($[\alpha]_D^{22}$ −13.6°) (Harborne et al., 1975). Thus, 1 is (−)-dihydrodaidzin or 7-O-β-D-glucopyranosyl-4'-hydroxy-isoflavanone.

Isoflavanone 2 gave $C_{21}H_{23}O_{10}$ by HRFABMS indicating the presence of one more oxygen atom than 1. The UV, IR, $^1$H- and $^{13}$C NMR spectra of 1 and 2 were almost identical, except for the presence of a hydroxyl-group singlet at δ 13.98 in 2, which disappeared on deuterium exchange (Talukdar et al., 2000). This functionality was further confirmed by a bathochromic shift of 9 nm in the UV spectrum in the presence of AlCl3. Two, meta-coupled doublets at δ 6.19 and 5.97 (2H, d, J=2.0 Hz) represented H-6 and H-8, respectively. 1H-1H DQF-COSY analysis showed three-spin-coupled systems resulting from the presence of substitutions at positions C-5, C-7 and C-4'. The specific rotation of $[\alpha]_D^{25}$−23.7° indicated that 2 is (−)-dihydrogenistin or 7-O-β-D-glucopyranosyl-5,7,4'-trihydroxyisoflavanone.

Isoflavone 3 gave $C_{26}H_{27}O_{11}$ by HRFABMS. The UV absorption at 272 nm, was typical for an isoflavone (Kitagawa et al., 1984; Mabry et al., 1970). 1H NMR revealed the characteristic chemical shifts and coupling patterns for a 7,4'-oxygenated isoflavone. The most downfield signal δ 7.98 (1H, d, J=8.7 Hz) was for H-5 which is peri to the C-4 carbonyl, while signals for H-6 and H-8 partially overlapped to appear as a multiplet centered at δ 6.97. Signals for a 4'-O-methyl group (δ 3.94), a 7-O-linked glucosyl unit, and two acetyl methyl group singlets (δ 1.95 and 2.07), all indicated that 3 was an acylated derivative of oninin (formononetin-7-O-β-D-glucopyranoside) (Lewis et al., 1998). The acetyl moieties were attached to positions 2" and 6", based on the $^1$H NMR shifts of protons attached to these positions versus free glucose (Tipson and Horton, 1983). Characteristic correlations observed between the glucosyl anomeric proton (δ 5.05) and H-8 in the DQF-COSY spectrum and the quaternary aromatic carbon at (δ 164.50) by HMBC confirmed the C-7 glucose linkage. The methoxyl group singlet (δ 3.94) of 3, was correlated with the C-4' carbon at (δ 161.00) by HMBC. HMBC correlations between the two acetyl moieties and the oxygenated H-2 and H-6 of the glucose core ($^1$H/$^{13}$C/$^1$H: δ 1.95/170.40/4.36, C-2" acetyl; and δ 2.07/172.80/4.66/4.83, C-6" acetyl) confirmed the sites of acylations. Therefore, 3 was identified as the new compound, formononetin-7-O-(2",6"-O-diacetyl) glucopyranoside, (2",6"-O-diacetyloninin).

Saponin 13 gave m/z1243.6110 for $C_{59}H96NaO_{26}$ by HRFABMS. Negative-ion FABMS indicated the loss of one pentose, one hexose, two deoxyhexoses, and one glucuronic acid residue. Acid hydrolysis of 13 furnished the aglycone and monosaccharide components, glucuronic acid, galactose, rhamnose and arabinose by TLC analysis. The sugars of 13 were evidenced by five anomeric proton and carbon signals in 1H and 13C NMR spectra (Table 4). By $^{13}$C NMR, the two methyl carbon signals at δ 18.80 and 18.00 and proton signals at δ 1.24 and 1.28 (3H each, d, J=6.5 Hz) indicated that 13 contained two 6-deoxy sugars. By $^{13}$C NMR, all of the monosaccharides were pyranoses. The anomeric configurations were fully defined from their $^3J_{H1-H2}$ coupling constants as well as from NOE correlations observed in the ROESY spectrum (Hosny et al., 1999).

The anomeric configurations were fully defined from their $3J_{H1-H2}$ and $1JC_{H1-H2}$ coupling constants (Table 4) as well as from NOE correlations observed in the ROESY spectrum. The β-anomeric configurations for the glucuronic acid and galactose residues were evident from correlations between H-1 and H-5. The $J_{H-H}$ values of 7.8 and 8.2 Hz for glucuronic acid and galactose, respectively, provided further evidence for their β-configurations. The small $3_{JH1-H2}$ coupling constants of 1.5 and 1.6 Hz, the three-bond HMBC couplings between the anomeric protons and C-3 and C-5, and NOE relationships between H-1 and H-3, H-1 and H-5 in ROESY spectra all indicated α-orientations for the two rhamnoses. The presence of an α-L-arabinopyranoside was shown by a $J_{H1-H2}$ coupling constant of 6.5 Hz, and the ROESY spectrum, which showed NOEs from H-1 to H-2, and H-3 to H-5 as expected for an α-L-arabinopyranoside in rapid 4C1⇌1C4 conformational exchange (Jia et al., 1998; De Tommasi et al., 1998).

DEPT NMR analysis indicated 30 methines, 12 methylenes, 9 methyl groups and by difference from the broad-band spectrum, 8 quaternary carbon atoms for 13 (Table 4). Twenty eight sp³, and two sp² carbon signals by $^{13}$C NMR, and seven methyl group singlets and a broad triplet vinyl proton by $^1$H NMR confirmed that the aglycon possessed an olean-12-ene skeleton (Arao et al., 1997). EIMS, and detailed 2D NMR analyses using DQF-COSY, ROESY, HMQC and HMBC identified the aglycon as soysapogenol B (Table 4), a common aglycon of soybean triterpenoid glycosides, including one compound previously identified by us from soy molasses (Hosny and Rosazza, 1999; Taniyama et al., 1988; Kitagawa et al., 1984). Downfield shifts in $^{13}$C NMR for C-3 (δ 89.30) and C-22 (δ 84.95) versus soyasapogenol B, suggested 13 was a bisdesmosidic glycoside containing sugars at both of these positions.

A combination of 1H-1H DQF-COSY, ROESY and HMQC NMR studies confirmed connectivites between, C-3-C-2-C-1 for ring A, C-5-C-6-C-7 for ring B, C-9-C-11-C-12 for ring C and C-16-C-15 for ring D. Assignments of the C-6/C-7 and C-15/C-17 methylene protons were confirmed by observed couplings between H-7 (axial) and 3H-26, and between H-15 (axial) and 3H-27. Extensive use of HMBC correlations among seven methyl-groups and the 24-methylenes made it possible to confirm the ring system of the aglycone (Hosny and Rosazza, 1999; Taniyama et al., 1988; Kitagawa et al., 1984). From the HMQC spectrum, C-5 (δ 55.14) was correlated with H-5 (δ 1.44), while C-6 (δ 18.80)

was related to H-6α (δ 1.90). H-6α could also be related to H-5α (δ 1.44) and H-7α (δ 1.60) by DQF-COSY. Similarly, C-16 (δ 28.17) was correlated with H-16α (δ 2.05). By DQF-COSY H-16α was correlated with H-15β (δ 1.39). By HMQC, C-12 (δ 122.83) was correlated with H1-12 (δ 5.66) which in turn was related to H-11 (δ 1.86) by DQF-COSY.

The position of the trisaccharide moiety was unambiguously defined by HMBC and ROESY studies. A significant cross-peak due to long-range correlation between C-3 (δ 89.30) of the aglycon and H-1 (δ 5.12) of glucuronic acid indicated that the glucuronic acid residue was linked to C-3 of the aglycon. A cross-peak between H-1 (δ 5.30) of galactose and C-2 (δ 80.95) of glucuronic acid, and a cross-peak between H-1 (δ 5.22) of rhamnose and C-2 (δ 78.57) of galactose identified the trisaccharide as β-fabatriosyl (Arao et al., 1997). Similarly, the sequence of the disaccharide chain at C-22 was deduced from long-range correlations of H-1 (δ 5.37) of rhamnose with C-2 (δ 82.70) of arabinose. Correlation between C-22 (δ 84.95) of the aglycon and H-1 (δ 5.18) of arabinose indicated the attachments of terminal sugar moieties to the aglycon. The two sugar chains of 13 were also deduced from the following key nuclear Overhauser effect (NOE) correlations observed in the ROESY spectrum: H-1 (δ 5.22) of rhamnose with H-2 (δ 4.76) of galactose, H-1 (δ 5.30) of galactose with H-2 (δ 4.65) of glucuronic acid and H-1 (δ 5.37) of rhamnose with H-2 (δ 4.60) of arabinose. Thus, the structure of saponin 13 was established as 3-O-{[α-L-rhamnopyranosyl-(1→2)-β-D-galactopyranosyl-(1→2)-β-D-glucurono-pyranosyl}-22-O-[α-L-rhamnopyranosyl-(1→2)-α-L-arabinopyranosyl] 3β,22β,24-trihydroxyolean-12-ene.

Saponin 14 gave m/z 1273.6189 for $C_{60}H_{98}NaO_{27}$ by HRFABMS. 2D NMR spectral data (Table 4) was nearly identical to that for 13, except for the disaccharide chain at C-22 of the aglycon. A β-D-gluopyranosyl unit was present in 14 versus an α-L-arabinopyranosyl unit in 13. By use of a combination of DQF-COSY, HMQC, HMBC and ROESY (Table 4), the structure of saponin 14 was established as 3-O-{[α-L-rhamnopyranosyl-(1→2)-β-D-galactopyranosyl-(1→2)-β-D-glucurono-pyranosyl}-22-O-[α-L-rhamnopyranosyl-(1→2)-β-D-glucopyranosyl] 3β,22β,24-trihydroxyolean-12-ene.

Example 3

Materials and Methods

Flash column liquid chromatography was performed using J. T. Baker glassware with 40-μm silica gel (Baker) and Sepralyte $C_{18}$ (40 μm) as the stationary phase. TLC was carried out on precoated silica gel 60 $F_{254}$ (Merck) plates. Developed chromatograms were visualized by fluorescence quenching under 245-nm UV light and by spraying with diazotized sulfanilic acid spray reagent. The reagent was freshly prepared by mixing equal volumes of 0.5% $NaNO_2$ and 0.5% sulfanilic acid in 2% HCl. Plates were sprayed with this mixture followed by spraying with 5% NaOH in 50% ethanol and warming with a heat gun for 3 min for isoflavonoids. For saponins, chromatograms were visualized by spraying developed plates with 1% vanillin/$H_2SO_4$, followed by heating at 100° C. for 5 min. TLC plates were developed with solvent systems: A ($CHCl_3$:MeOH:$H_2O$, 80:20:2, v:v:v), B (EtOAc: MeOH:$H_2O$, 100:16.5:13.5), C($CHCl_3$:MeOH:$H_2O$, 61:32:7).

The HPLC system (Shimadzu, Columbia, Md.) consisted of a solvent delivery system equipped with dual pumps (LC-10 AD), an in-line degasser (DGU-14A), a quaternary solvent mixer (FCV-10A), a photodiode array (PDA) ultra violet-visible detector (SPD-M6A) and a sample auto-injector (SIL-10A), connected to a system controller (SCL-10A VP). Data acquisition and processing were controlled by a Shimadzu SPD-M6A program (Version 2.0) running on an IBM Aptiva C3E Pentium computer (IBM, Stamford, Conn.) attached to a cannon BJC-620 color bubble jet printer (Costa Mesa, Calif.). Standard compounds and sample mixtures were resolved over a 250 mm×4.6 mm I.D. Econosil $C_{18}$ (particle size 10 μ) column and eluted a flow rate 1.0 mL/min when analyzing standards and SPC mixtures. The following gradients were used for all separations: solvent A was $CH_3CN$:$H_2O$:HCOOH (10:90:5, v/v/v) and solvent B was composed of $H_2O$: $CH_3CN$:HCOOH, (10:90:5, v/v/v). Gradient conditions were 0–3 min 0% B; 3–4 min 0–17% B; 4–22 min 17–28% B; 22–23 min 28–50 % B, 23–45 min 50% B. HPLC samples were detected at a wavelength of 260 nm. Sample injection volumes varied between 2.5–20 μg depending upon sample concentrations.

The HPLC retention volumes ($R_v$) in milliliters for isoflavone standards (Hosny and Rosazza, 1999) and isolated compounds were: dihydrodaidzin (1) (13.89), daidzin (8) (15.28), genistin (9) (15.64), daidzein-7-O-β-D-(6"-O-acetylglucopyranoside (11) (16.18), dihydrogenistin (2) (16.92), glycitin (10) (17.34), genistein-7-O-β-D-(6"-O-acetylglucopyranoside (12) (18.31), ononin (Indofine Chemical Company, Inc.) (18.85), formononetin-7-O-(2", 6"-O-diacetyl) glucopyranoside (3) (21.14), glycitein (6) (22.04), sissotrin (Indofine Chemical Company, Inc.) (25.92), daidzein (4) (26.47) genistein (5) (31.08), formononetin (31.39), biochanin A (7) (39.88).

Optical rotations were measured with a JASCO P-1020 polarimeter. UV spectra were determined with a Hitachi 340 spectrophotometer. IR spectra ($cm^{-1}$) were obtained using a Nicolet 205 FT-IR spectrometer connected to a Hewlett-Packard Color Pro plotter. High resolution Fast Atom Bombardment mass spectra (HRFABMS) were taken on a VG-ZAB-HF reversed geometry (BE configuration, where B is a magnetic sector and E is an electrostatic analyzer) mass spectrometer (MS) (VG Analytical, Inc.).

NMR spectra were obtained in DMSO-$d_6$ or $CD_3OD$ using TMS as the internal standard, with chemical shifts expressed in (δ) and coupling constants (J) in Hz. Routine $^1H$ and $^{13}C$ NMR spectra were obtained with a Bruker NMR 400 (Bruker Instruments, Billerica, Mass.), operating at 400 MHz ($^1H$) and 100 MHz ($^{13}C$). DQF-COSY, ROESY, HMBC and HMQC NMR studies were carried out using a Bruker AMX-600 high-field spectrometer equipped with an IBM Aspect-2000 processor and with software VNMR version 4.1.

The following materials and reagents were used for cell culture and cytotoxic assays. Human stomach carcinoma (Hs 740.T, Hs 756 T), breast adenocarcinoma (Hs 578 T, Hs 742.T) and prostate carcinoma (DU 145, LNCaP-FGC) cell lines were purchased from the American Type Culture Collection ATCC. Dulbecco's modified Eagle medium (DMEM) (Gibco, Grand Island, N.Y.), Eagle Minimum Essential Medium (EMEM) and Rosewell Park Memorial Institute (RPMI) 1640 medium were from Nissui Pharm. Co., Ltd., Tokyo, Japan. Flat-bottom plates, 96-well were from Iwaki Glass Co., LTD (Funabashi-Chiba-Ken, Japan). The 3-[4,5-dimethlthiazol-2-yl]-2,5-diphenyltetrazolium bromide (MTT) colorimetric assay (Goren et al., 1996; Rubinstein et al., 1990) was from Sigma (St. Louis, Mo., USA), and 10% fetal bovine serum FBS was from Gibco BRL (Rockville, Md., USA). All other chemicals used were of analytical reagent grade.

Example 4

Extraction and Isolation

SPC powder (725 g) was exhaustively extracted at room temperature with MeOH (3×5L). The combined MeOH extracts were concentrated in vacuo at 30° C. to a brown residue (272 g). The concentrated extract was suspended in $H_2O$ (150 mL) and filtered through Celite 545 (Fisher Scientific). The filtrate and $H_2O$ washings (500 mL) were combined and washed with n-hexane (3×500 mL). The aqueous fraction (435 mL) was concentrated in vacuo to give a crude extract of (186 g) that was partitioned first with EtOAc (3×2 L) and then with n-BuOH (3×2 L). The EtOAc extract (64 g) was fractionated by Si gel flash column chromatography (2.5×62 cm) using in sequence, $CH_2Cl_2$-MeOH (90:10→50:50). Twelve fractions were combined based on TLC using solvent systems A, B and C. Subsequent purification of chromatographically similar fractions were accomplished by Sephadex LH-20 column chromatography using gradients of $CH_3OH$ in $CH_2Cl_2$ ranging from 30→70%. Alternatively, fractions were resolved by reversed phase, Sepralyte $C_{18}$ flash column chromatography (1.5×50 cm), using a $H_2O$-MeOH gradient solvent system (20→50%) at a flow rate of 3 mL min. Final sample purifications were carried out with Sephadex LH-20 (25–150 µm, Pharmacia Fine Chemical Co.) columns eluted with MeOH to afford compounds 1 (58 mg), 2 (92 mg), 3 (28 mg), 4 (42 mg), 5 (95 mg), 6 (18 mg), 7 (13 mg), 8 (54 mg), 9 (83 mg), 10 (15 mg), 11 (264 mg), and 12 (285 mg).

The n-BuOH extract was concentrated in vacuo at 30° C. and the residue (26 g) was dissolved in 10 mL $H_2O$ and chromatographed over a Diaion HP-20 (Mitsubishi Kasei Co., Ltd., Tokyo, Japan) column (3.5×90 cm) eluted with $H_2O$ initially, with increasing concentrations of MeOH while being monitored by TLC (solvent systems B and C). Fractions were grouped as A, ($H_2O$, 5.170 g), B (25% MeOH/$H_2O$, 3.785 g), C (50% MeOH/$H_2O$, 2.550 g), D (75% MeOH/$H_2O$, 1.620 g). Fraction A (5.170 g) was rechromatographed over polyamide (SC6, Machery-Nagel, Düren, Germany 3.5×90 cm), and fractions eluting with 20 and 30% aqueous MeOH were combined separately for further Si gel, flash column chromatography using ($CH_2Cl_2$:MeOH:$H_2O$, 90:10:1→60:40:10) and repeated reversed-phase, Sepralyte $C_{18}$ flash column chromatography, using a $H_2O$-MeOH gradient solvent system (10→40%, 3 mL min) to afford 13 (28 mg) and 14 (37 mg). Fractions B and C were chromatographed again over a Si gel flash column (2.5×62 cm) using ($CHCl_3$:MeOH:H2O 80:20:1→60:40:4) to yield three further fractions, B1, B2 from the B fraction and C-1 from C. Fraction B1 (525 mg) was subjected to Sepralyte $C_{18}$ flash column chromatography using a $H_2O$: MeOH gradient solvent system (10→30%, 3 mL min) to afford 15 (35 mg). Similarly, fraction B-2 (440 mg) and fraction C-1 (378 mg) were separately subjected to Sepralyte $C_{18}$ column chromatography with the same solvent as for 15 and further purified by Sephadex LH-20 eluted with MeOH to afford 16 (26 mg) and 17 (16 mg).

Example 5

Cytotoxicity Assay

Cell lines Hs 740.T, Hs 746 T, Hs 578 T and Hs 742.T were cultured in Dulbecco's Modified Eagle's Medium (DMEM) containing 10% heat-inactivated Fetal Bovine Serum (FBS). The DU 145 cells were cultured in Eagle Minimum Essential Medium (EMEM) containing Earle's salts and supplemented with amino acids and 10% heat-inactivated FBS. The LNCaP-FGC cell lines were maintained in Rosewell Park Memorial Institute (RPMI) 1640 medium containing 10% heat-inactivated FBS. All cell lines were cultivated in an incubator at 37° C. in humidified air containing 5% $CO_2$. For routine cytotoxicity assays, all six cell lines were adapted to one single medium RPMI 1640 medium supplemented with 10% FBS, 2 mM L-glutamine, penicillin (100 units/mL) and streptomycin (100 µg/mL). For the microassay, the growth medium was supplemented with 10 mM HEPES (1-(2-hydroxyethyl) piperazine-4-ethanesulfonic acid) buffer (pH 7.3) and incubated at 37° C. in a $CO_2$ incubator. These methods are similar to those used by Goren et al., (1996) AND Rubinstein et al., (1990).

Cellular viability in the presence and absence of experimental agents was determined using the standard MTT (3-[4,5-dimethlthiazol-2-yl]-2,5-diphenyltetrazolium bromide) calorimetric assay (Goren et al., 1996; Rubinstein et al., 1990). The assay is based on reduction of MTT by the mitochondrial dehydrogenase of viable cells to give a blue formazan product that can be measured spectrophotometrically (Goren et al., 1996; Rubinstein et al., 1990). In brief, exponentially growing cells were harvested, and 200 µL cells suspension were seeded in 96-well microplates and preincubated for 24 h at 37° C. under 5% $CO_2$ to allow cell attachment. After attachment, 10 µL of an EtOH: $H_2O$ (1:1 solution) containing varying concentrations of test samples were added to wells in duplicate, and 10 µL EtOH:$H_2O$ (1:1) was added into wells as a control. Sample containing microplates were further incubated for 6 days. Cell survival was evaluated by adding 10 µL of 5 mg mL of MTT in 0.1 mM, pH 7.4 phosphate buffered saline to each well, and reincubating plates in 5% $CO_2$/air for 4 h at 37° C. Plates were then centrifuged at 1,500×g for 5 min to precipitate cells and MTT formazan. An aliquot of 100 µL of the supernatant was removed, and DMSO (100 µL) was added to dissolve the precipitated, reduced MTT. The plate was mixed on a microshaker for 10 min, and the absorbance was determined at 550 nm with a multiwell scanning spectrophotometer (Dynex MR 5000, Chantilly Va.). The $ED_{50}$ value, which reduces the viable cell number was defined as the concentration of test samples resulting in a 50% reduction of absorbance compared to untreated controls (Goren et al., 1996; Rubinstein et al., 1990).

The 50% effective doses (ED50) obtained by measuring growth inhibition with MTT (3-[4,5-dimethlthiazol-2-yl]-2,5-diphenyltetrazolium bromide]) (Goren et al., 1996; Rubinstein et al., 1990) are shown in Table 3. As can be seen, cell lines LNCAP-FGC and HS742.T were the least sensitive of all lines examined to the activities of these compounds. The activities observed with crude extracts was surprising. While none gave activities surpassing those of pure compounds, these extracts contain mixtures of compounds that could function together synergistically in displaying cytotoxicity. Of the isoflavonoids, less polar isoflavones 3 and 5 were generally more potent than isoflavanones 1 and 2. This suggests the importance of the C2–C-3 double bond for cytotoxicities in these cell lines. In general soy saponins 13–17 were more cytotoxic than the isoflavonoids 1–3 and 5 with these cell lines. Soy saponins 13, 14 and 15 were more cytotoxic vs both stomach carcinomas, the Hs 578 T breast adenocarcinoma and the DU 145 prostate carcinoma lines. All three compounds are C-22-glycosides, whereas the less active 16 and 17 glycosides possess free hydroxyl groups at C-22.

The results suggest a slight enhancement of cytotoxicity when this position is glycosylated. Relatively limited information exists on the structure-activity-relationships for the cytotoxicities of these classes of compounds. Although it is not possible to establish a conclusive structure-activity-relationships with the small number of compounds evaluated here, the results provide insight as to structural moieties that modulate cytotoxic activity, and add to existing knowledge on the cytotoxicities of these classes of compounds. In summary, the findings confirm the work of others (Zhou et al., 1999; Arao et al., 1997; Rao et al., 1997; Peterson and Barnes, 1991; Jing et al., 1993; Yanagihara et al., 1993; Naik et al., 1994; Choi et al., 1998; Menon et al., 1998; Zhou et al., 1998; Pool-Zobel et al., 2000; Rao and Sung, 1995) in showing that soy phytochemical concentrate extracts, isoflavonoids and soy saponins have direct effects on human stomach, breast and prostate carcinoma cell lines in vitro.

(1H, t, J=4.9 Hz, H-3), 7.38 (1H, d, J=8.6 Hz, H-5), 6.69 (1H, dd, J=2.2, 8.6 Hz, H-6), 6.51 (1H, d, J=2.2 Hz, H-8), 7.15 (2H, d, J=8.6 Hz, H-2', 6'), 6.82 (2H, d, J=8.6 Hz, H-3', 5'); glucosyl moiety: δ 5.12 (1H, d, J=7.8 Hz, H-1"), 3.45 (1H, dd, J=7.8, 9.2 Hz, H-2"), 3.54 (1H, t, J=9.2 Hz, H-3"), 3.50 (1H, t, J=9.2 Hz, H-4"), 3.39 (1H, m, H-5"), 3.72 (1H, dd, J=12.0, 3.4 Hz, H-6"A), 3.86 (1H, dd, J=12.0, 5.6 Hz, H-6"B); $^{13}$C NMR (DMSO-d$_6$, 100 MHz) aglycon δ 71.34 (C-2), 47.19 (C-3), 198.40 (C-4) 129.00 (C-5), 116.30 (C-6), 164.60 (C-7), 104.90 (C-8), 155.20 (C-9) 117.80 (C-10),

TABLE 3

Cytotoxicity of soybean extracts and isolated compounds against breast, prostate and stomach tumor cell lines.

| Extract Compound | Stomach Carcinoma | | ED$_{50}$ (μg/mL) Breast Adenocarcinoma | | Prostate Carcinoma | LNCAp- |
|---|---|---|---|---|---|---|
| | Hs 740.T | Hs 746 T | Hs 578 T | HS 742.T | DU 145 | FGC |
| MeOH | 12.32 (±0.27) | 8.45 (±0.18) | 17.11 (±0.38) | 45.29 (±0.73) | 7.15 (±0.12) | 42.18 (±0.72) |
| EtOAc | 10.78 (±0.24) | 11.57 (±0.25) | 8.84 (±0.17) | 38.19 (±0.61) | 3.94 (±0.07) | 37.77 (±0.58) |
| n-BuOH | 8.89 (±0.19) | 9.43 (±0.15) | 5.22 (±0.09) | 29.15 (±0.52) | 4.59 (±0.09) | 30.53 (±0.55) |
| Isoflavonoids | | | | | | |
| 1 | 17.37 (±0.43) | 14.92 (±0.30) | 28.23 (±0.52) | 33.57 (±0.55) | 9.16 (±0.17) | 32.45 (±0.59) |
| 2 | 15.12 (±0.34) | 12.24 (±0.28) | 15.36 (±0.30) | 30.80 (±0.50) | 10.25 (±0.20) | 41.58 (±0.68) |
| 3 | 7.61 (±0.10) | 8.89 (±0.18) | 5.44 (±0.10) | 25.53 (±0.44) | 4.18 (±0.06) | 22.12 (±0.37) |
| 5 | 4.38 (±0.07) | 5.82 (±0.09) | 3.50 (±0.05) | 14.88 (±0.22) | 2.39 (0.04) | 25.45 (±0.39) |
| Saponins | | | | | | |
| 13 | 3.53 (±0.05) | 2.47 (±0.04) | 2.39 (±0.03) | 17.51 (±0.29) | 3.12 (±0.05) | 27.50 (±0.0.43) |
| 14 | 4.10 (±0.05) | 3.94 (±0.05) | 2.12 (±0.02) | 14.63 (±0.25) | 3.25 (±0.05) | 24.10 (±0.35) |
| 15 | 3.15 (±0.04) | 3.22 (±0.05) | 4.84 (±0.09) | 30.10 (±0.53) | 2.11 (±0.02) | 30.70 (±0.50) |
| 16 | 8.97 (±0.11) | 7.36 (±0.13) | 9.87 (±0.15) | 31.55 (±0.58) | 5.75 (±0.10) | 40.68 (±0.62) |
| 17 | 9.61 (±0.15) | 9.59 (±0.12) | 8.77 (±0.10) | 28.68 (±0.48) | 9.13 (±0.16) | 37.29 (±0.60) |

Values are presented as mean ± SE of 2 test sample observation, compared with that of control group (p < 0.05) for all values.

Example 6

Statistical Analysis

All cytotoxic data were expressed as mean±SE. Student's t-test (Woodson, 1987) was applied for detecting the Significance of difference between each sample. p<0.05 was taken as the level of significance.

Example 7

Compound 1

The compound was obtained as a yellow, amorphous powder (58 mg); $[\alpha]^{22}_D$ −12.9° (c 1.00, MeOH); UV (MeOH) $\lambda_{max}$ (log ε) 276 (4.27), 310 (4.08), +NaOMe 318, +AlCl$_3$ 308, +HCl 308, +NaOAc 277 nm; IR (KBr) $v_{max}$ 3420, (OH), 1710 (C=O), 1590 (aromatic ring) cm$^{-1}$; $^1$H NMR (DMSO-d$_6$, 600 MHz) aglycon δ 4.86 (1H, dd, J=4.9, 12.2 Hz, H-2a), 4.97 (1H, dd, J=7.2, 12.2 Hz, H-2b), 3.91

128.70 (C-1'), 131.40 (C-2', 6'), 159.20 (C-4'), 116.20 (C-3', 5'); glucosyl moiety δ101.20 (C-1"), 74.60 (C-2"), 77.70 (C-3"), 71.11 (C-4"), 78.22 (C-5"), 62.31 (C-6"); HRFABMS, m/z 419.1346 [M+H]$^+$ (calcd for C$_{21}$H$_{23}$O$_9$, 419.1342).

Example 8

Compound 2

The compound was obtained as a yellow, amorphous powder (92 mg); $[\alpha]^{25}_D$ −23.7° (c 0.50, MeOH); UV (MeOH) $\lambda_{max}$ (log ε) 272 (4.36), 308 (3.95), +NaOMe 314, +AlCl$_3$ 317, +HCl 319, +NaOAc 271 nm; IR (KBr) $v_{max}$ 3435, (OH), 1695 (C=O), 1595 (aromatic ring) cm$^{-1}$; $^1$H NMR (DMSO-d$_6$, 600 MHz) aglycon δ 4.77 (1H, dd, J=5.1, 12.1 Hz, H-2a), 4.88 (1H, dd, J=7.0, 12.1 Hz, H-2b), 3.90 (1H, t, J=5.1 Hz, H-3), 6.19 (1H, d, J=2.0 Hz, H-6), 5.98 (1H, d, J=2.0 Hz, H-8), 7.43 (2H, d, J=8.6 Hz, H-2', 6'), 6.89 (2H, d, J=8.6 Hz, H-3', 5'), 13.98 (1H, br s, HO-5); glucosyl moiety δ 5.08 (1H, d, J=7.8 Hz, H-1"), 3.39 (1H, dd, J=7.8, 9.1 Hz, H-2″), 3.52 (1H, t, J=9.1 Hz, H-3″), 3.48 (1H, t, J=9.2 Hz, H-4″), 3.42 (1H, m,H-5″), 3.65 (1H, dd, J=11.9, 3.5 Hz, H-6″A), 3.79 (1H, dd, J=11.9, 6.2 Hz, H-6″B); $^{13}$C NMR (DMSO-d$_6$, 100 MHz) aglycon δ 71.26 (C-2), 47.10 (C-3), 197.86 (C-4) 164.50 (C-5), 102.10 (C-6), 169.00 (C-7), 96.35 (C-8), 165.40 (C-9) 103.10 (C-10), 128.60 (C-1′), 133.10 (C-2′, 6′), 159.00 (C-4′), 117.50 (C-3′, 5′); glucosyl moiety δ 98.29 (C-1″), 74.76 (C-2″), 77.67 (C-3″), 71.02 (C-4″), 78.11 (C-5″), 62.43 (C-6″); HRFABMS, m/z 435.1297 [M+H]$^+$ (calcd for C$_{21}$H$_{23}$O$_{10}$, 435.1291).

Example 9

Compound 3

The compound was obtained as a yellow, amorphous powder (28 mg); [α]$^2$$_D$+9.3° (c 0.55, MeOH); UV (MeOH) λ$_{max}$ (log ε) 238 (4.12), 272 (4.48), +NaOMe 296, +AlCl$_3$ 276, +HCl 278, +NaOAc 279 nm; IR (KBr) ν$_{max}$ 3400, (OH), 1735 (acetyl), 1710 (C=O), 1595 (aromatic ring) cm$^{-1}$; $^1$H NMR (DMSO-d$_6$, 600 MHz) aglycon δ 8.20 (1H, s, H-2), 7.98 (1H, d, J=8.7 Hz, H-5), 6.97 (2H, m, H-6, 8), 7.38 (2H, d, J=8.7 Hz, H-2′, 6′), 7.08 (2H, d, J=8.7 Hz, H-3′, 5′), 3.94 (3H, s, MeO-4′); glucosyl moiety δ 5.05 (1H, d, J=7.7 Hz, H-1″), 4.36 (1H, dd, J=7.7, 9.1 Hz, H-2″), 3.58 (1H, t, J=9.1 Hz, H-3″), 3.40 (1H, t, J=9.1 Hz, H-4″), 3.72 (1H, m, H-5″), 4.66 (1H, dd, J=11.9, 3.2 Hz, H-6″ A), 4.83 (1H, dd, J=11.9, 6.4 Hz, H-6″B), 1.95 (3H, s, AcO-2″), 2.07 (3H, s, AcO-6″); $^{13}$C NMR (DMSO-d$_6$, 100 MHz) aglycon δ 153.30 (C-2), 123.60 (C-3), 176.70 (C-4) 128.72 (C-5), 111.20 (C-6), 164.50 (C-7), 104.90 (C-8), 158.00 (C-9) 117.25 (C-10), 123.20 (C-1′), 131.36 (C-2′, 6′), 161.00 (C-4′), 114.58 (C-3′, 5′); glucosyl moiety δ 101.20 (C-1″), 77.84 (C-2″), 72.55 (C-3″), 73.05 (C-4″), 71.77 (C-5″), 64.33 (C-6″), 170.40, 20.25 (AcO-2″), 172.80, 20.90 (AcO-6″), 56.75 (MeO-4′); HRFABMS, m/z 515.1550 [M+H]$^+$ (calcd for C$_{26}$H$_{27}$O$_{11}$, 515.1553).

Example 10

Compounds 4–12

The compounds gave UV, IR, $^1$H and $^{13}$C NMR, and FABMS data for [M+H]$^+$ ions in good agreement with reported data for daidzein (4) (C$_{15}$H$_{10}$O$_4$ [M+H]$^+$, 254) (Hosny and Rosazza, 1999); genistein (5) (C$_{15}$H$_{10}$O$_5$,[M+H]$^+$, 270) (Hosnay and Rosazza, 1999); glycitein (6) C$_{16}$H$_{13}$O$_5$, [M+H]$^+$, 285) (Hosny and Rosazza, 1999); biochanin A(7) (C$_{16}$H$_{13}$O$_5$ [M+H]$^+$, 285) (Tezuka et al., 2000); daidzin (8) (C$_{21}$H$_{21}$O$_9$[M+H]$^+$, 417) (Hosny and Rosazza, 1999); genistin (9) (C$_{21}$H$_{21}$O$_{10}$ [M+H]$^+$, 433) (Hosny and Rosazza, 1999); glycitin (10) (C$_{22}$H$_{23}$O$_{10}$ [M+H]$^+$, 447) (Tezuka et al., 2000); daidzein 7-O-β-D-(6″-O-acetylglucopyranoside) (11) (C$_{23}$H$_{23}$O$_{10}$ [M+H]$^+$, 459) (Chang et al., 1994); and genistein 7-O-β-D-(6″-O-acetylglucopyranoside) (12) (C$_{23}$H$_{23}$O$_{11}$ [M+H]$^+$, 475) (Chang et al., 1994).

Example 11

Compound 13

The compounds was obtained as a white amorphous powder (28 mg); [α]$^{25}$$_D$ –14.20° (c 0.50, MeOH); IR (KBr) ν$_{max}$ 3395, (OH), 1632 (C=C) cm$^{-1}$; $^1$H and $^{13}$C NMR (Table 4); HRFABMS m/z 1243.6110 [M+Na]$^+$ (calcd for C$_{59}$H$_{96}$NaO$_{26}$, 1243.6107); negative ion FABMS m/z 1087 [M−H-arabinose]$^-$, 1073 [M−H-rhamnose]$^-$, 1057 [M−H-galactose]$^-$, 911 [M−H-rhamnose-galactose]$^-$, 735 [M−H-rhamnose-galactose-glucuronic acid].

TABLE 4

1D and Selected 2D NMR Chemical Shift Assignments of Aglycon and Sugar Moieties of Saponins 13 and 14 (CD$_3$OD), 600 MHz for $^1$H and 100 MHz for $^{13}$C NMR

| position | 13 | | 14 | | | | | |
|---|---|---|---|---|---|---|---|---|
| | $^1$H (J in Hz) | $^{13}$C | $^1$H (J in Hz) | $^{13}$C | DEPT | DQF-COSY | ROESY | HMBC |
| aglycon | | | | | | | | |
| 1α | 1.12 dt, (12.5, 4.5) | 39.22 | 1.09 dt, (11.5, 4.0) | 38.81 | CH$_2$ | H-1β, 2α, 2β | H-1β, 9α | Me-25 |
| 1β | 1.84 m | — | 1.72 m | — | — | H-1α, 2α, 2β | H-11, Me-25 | Me-25 |
| 2α | 2.31 dt, (12.5, 4.5) | 26.20 | 2.25 dt, (11.5, 4.0) | 26.75 | CH$_2$ | H-1α, 1β, 2β, 3α | H-2β | C-4, 10 |
| 2β | 2.11 dq, (4.5, 12.5) | — | 2.08 dq, (4.0, 11.5) | — | — | H-1β, 2α, 3α | Me-25 | C-4 |
| 3α | 3.78 dd (12.5, 4.5) | 89.30 | 3.65 dd (11.5, 4.0) | 88.58 | CH | H-2α, 2β | H-5α, Me-23, glcA-1 | C-1, 2, 4, 5, Me-23, 24, glcA-1 |
| 4 | — | 41.83 | — | 41.80 | C | — | — | — |
| 5α | 1.44 d, (12.5) | 55.14 | 1.62 d, (11.5) | 55.48 | CH | H-6β, 7α, 7β | 6α, 9α, Me-23 | C-3, Me-23, 24, Me-25 |
| 6α | 1.90 d, (12.5) | 18.80 | 1.75 m | 19.15 | CH$_2$ | H-6β, 7α, 7β | Me-23 | C-4, 8, 10 |
| 6β | 1.35 m | — | 1.49 m | — | — | H-5α, 6α, 7α, 7β | H-7β, Me-26 | C-5, Me-26 |
| 7α | 1.60 dt, (12.0, 3.8) | 32.12 | 1.67 dt, (11.5, 4.0) | 33.00 | CH$_2$ | H-5α, 6α, 6β, 7β | H-7β | C-5, Me26 |
| 7β | 1.21 d, (12.0) | — | 1.28 d, (11.5) | — | — | H-5α, 6α, 6β, 7α | H-7α, | C-8, 14, Me26 |
| 8 | — | 40.75 | — | 40.66 | C | — | — | — |
| 9α | 2.16 dd (13.0, 8.0) | 47.64 | 2.13 dd (13.2, 8.0) | 48.26 | CH | H-12, | H-1α, 11, Me-27 | C-5, 7, 8, 10, 11, 12, 14, Me-25, Me-26 |
| 10 | — | 37.60 | — | 37.28 | C | — | — | — |

TABLE 4-continued 1D and Selected 2D NMR Chemical Shift Assignments of Aglycon and Sugar Moieties of Saponins 13 and 14
(CD₃OD), 600 MHz for ¹H and 100 MHz for ¹³C NMR

| | 13 | | 14 | | | | | |
|---|---|---|---|---|---|---|---|---|
| position | ¹H (J in Hz) | ¹³C | ¹H (J in Hz) | ¹³C | DEPT | DQF-COSY | ROESY | HMBC |
| 11 | 1.86 m | 24.11 | 1.88 m | 24.45 | $CH_2$ | H-12 | H-1β, 9α, Me-25 | C-8, 9, 10, 13 |
| 12 | 5.66 s | 122.83 | 5.39 s | 122.56 | CH | H-9α, 11, 18β | H-19β | C-9, 14, 18 |
| 13 | — | 144.30 | — | 144.54 | C | — | — | — |
| 14 | — | 42.15 | — | 42.30 | C | — | — | — |
| 15α | 1.78 m | 26.95 | 1.83 m | 26.64 | $CH_2$ | H-15β, 16β | H-15β, 16β | C-13, 17, 18, Me-27 |
| 15β | 1.39 m | — | 1.42 m | — | | H-15α, 16β | H-15α, 16β, Me-26, Me-28 | C-17, Me-26, Me-27 |
| 16α | 2.05 m | 28.17 | 1.91 m | 27.76 | $CH_2$ | | | |
| 16β | 1.90 m | — | 1.86 m | — | | H-15α, 15β | H-15α, 15β, Me-28 | C-14, Me-28 |
| 17 | — | 39.32 | — | 38.25 | C | — | — | — |
| 18β | 2.42 dd, (14.0, 4.5) | 45.77 | 2.38 dd, (13.5, 4.0) | 43.86 | CH | H-19α, 19β | H-12, Me-28, Me-30 | C-14, 20, Me-28, Me-29 or Me-30 |
| 19α | 1.95 d, (12.0) | 45.18 | 2.00 d, (13.5) | 46.28 | $CH_2$ | H-18β, 19β | H-19β, Me-29 | C-13, 17, 18, 20, Me-29, Me-30 |
| 19β | 1.64 d, (12.0) | — | 1.73 d, (13.5) | — | — | H-18β, 19α, 21 | H-19α, Me-28, Me-30 | C-17, 18, 20, 21, Me-29 or Me-30 |
| 20 | — | 30.92 | — | 30.75 | C | — | — | — |
| 21α | 1.80 m | 37.24 | 1.77 m | 36.63 | $CH_2$ | H-21β, 22α | H-21β, Me-29 | |
| 21β | 1.55 m | — | 1.62 m | — | — | H-21α, 22α | H-21α, 22α, Me-28 | |
| 22α | 4.43 m | 84.95 | 4.30 m | 86.44 | CH | 21α, 21β | H-18β, 21α, 21β, ara-1 | C-16, 18, 20, Me-28, ara-1 |
| 23 | 1.12 s | 22.54 | 1.16 s | 22.00 | $CH_3$ | — | H-3α, 5α, 6α, 24 | C-3, 4, 5, 24 |
| 24 | 4.11 d, (11.0) 4.58 d, (11.0) | 63.67 | 4.27 d, (10.5) 4.40 d, (10.5) | 64.40 | $CH_2$ | H-24 | H-5α, 6α, Me-23 | C-3, 4, 5, Me-23 |
| 25 | 0.86 s | 15.70 | 0.80 s | 16.29 | $CH_3$ | — | H-1β | C-1, 5, 10 |
| 26 | 0.93 s | 16.53 | 0.95 s | 17.18 | $CH_3$ | — | H-11, 6β, 15β | C-7, 8, 9, 10, 14 |
| 27 | 1.18 s | 25.50 | 1.25 s | 25.65 | $CH_3$ | — | H-9α | C-8, 13, 14, 15 |
| 28 | 0.89 s | 21.15 | 0.85 s | 21.00 | $CH_3$ | — | H-15β, 19β, 21β | C-16, 17, 18, 22 |
| 29 | 1.03 s | 31.11 | 1.00 s | 32.20 | $CH_3$ | — | H-19α, 21α | C-19, 20, 21, Me-30 |
| 30 | 0.98 s | 27.85 | 0.98 s | 27.12 | $CH_3$ | — | H-18β, 19β, 21β | C-19, 20, 21, Me-29 |
| Sugar Moiety C-3 | | | | | | | | |
| glcA-1 | 5.12 d, (7.8) | 105.30 | 5.10 d, (8.0) | 104.85 | CH | glcA-2 | H-3α, Me-23 | C-3 |
| glcA-2 | 4.65 dd, (7.8, 9.0) | 80.95 | 4.54 dd, (8.0, 9.2) | 79.42 | CH | glcA-3, gal-1 | gal-1 | gal-1 |
| glcA-3 | 3.57 m | 76.17 | 3.50 m | 76.62 | CH | glcA-2 | glcA-2, glcA-4 | glcA-1, glcA-5 |
| gal-1 | 5.30 d, (8.2) | 102.73 | 5.20 d, (8.0) | 103.20 | CH | glcA-2 | glcA-2 | glcA-2 |
| gal-2 | 4.76 dd, (8.2, 8.0) | 78.57 | 4.62 dd, (8.0, 9.5) | 78.00 | CH | rha-1 | rha-1 | rha-1 |
| rha-1 | 5.22 d, (1.6) | 103.25 | 5.15 d, (2.1) | 103.50 | CH | gal-2 | gal-2 | gal-2 |
| rha-6 | 1.24 d, (6.5) | 18.80 | 1.22 d, (6.3) | 18.24 | $CH_3$ | — | — | — |
| C-22 | | | | | | | | |
| ara-1 | 5.18 d, (6.5) | 108.10 | — | — | CH | ara-2 | H-22, Me-28 | C-22 |
| ara-2 | 4.60 dd, (8.6, 6.5) | 82.70 | — | — | CH | rha-1 | rha-1 | rha-1 |
| glc-1 | — | — | 4.98 d, (7.7) | 105.00 | CH | rha-2 | H-22, Me-28 | C-22 |
| glc-2 | — | — | 4.18 dd, (7.7, 9.5) | 80.11 | CH | rha-1 | rha-1 | rha-1 |
| rha-1 | 5.37 d, (1.5) | 102.92 | 5.18 d, (2.0) | 102.33 | CH | glc-2 | glc-2 | glc-2 |
| rha-2 | 3.52 dd (3.5, 1.5) | 72.57 | 3.58 dd (3.1, 2.0) | 72.73 | CH | rha-2 | ara-2, rha-4 | ara-2, rha-4 |
| rha-6 | 1.28 d, (6.5) | 18.00 | 1.33 d, (6.0) | 17.80 | $CH_3$ | — | — | — |

Example 12

Compound 14

The compound was obtained as a white amorphous powder (37 mg); $[\alpha]^{25}_D$ −23.00° (c 0.53, MeOH); IR (KBr) $\nu_{max}$ 3450, (OH), 1638(C═C) $cm^{-1}$; ¹H and ¹³C NMR (Table 4); HRFABMS m/z 1273.6189 [M+Na]⁺ (calcd for $C_{60}H_{98}NaO_{27}$, 1273.6193); negative ion FABMS m/z 1103 [M−H-rhamnose]⁻, 1087 [M−H-glucose]⁻, 941 [M−H-rhamnose-galactose]⁻, 765 [M−H-rhamnose-galactose-glucuronic acid].

Example 13

Compound 15

The compound was obtained as a white amorphous powder (35 mg). IR (KBr), 3455 (OH), 1635(C═C) $cm^{-1}$; FABMS, m/z 1107 [M+H]⁺ 1129 [M+, Na]⁺ (calcd for $C_{53}H_{87}O_{24}$ 1107). By these and ¹H and ¹³C NMR, 15 was identified as soyasaponin A2 (Hosny and Rosazza, 1999; Farmakalidis and Murphy, 1985).

Example 14

Compound 16

The compound was obtained as a white amorphous powder (26 mg). IR (KBr), 3450 (OH), 1635 (C=C) cm$^{-1}$; FABMS, m/z 959 [M+H]+ 981 [M+Na]+ (calcd for $C_{48}H_{79}O_{19}$, 959). By these and $^1$H and $^{13}$C NMR, 16 was identified as soysaponin V (Kitagawa et al., 1985).

Example 15

Compound 17

The compounds was obtained as a white amorphous powder (16 mg). IR (KBr), 3455 (OH), 1632(C=C) cm$^{-1}$; FABMS, m/z 635 [M+H]$^+$ 657 [M+Na]+ (calcd for $C_{63}H_{59}O_9$, 635). By these and $^1$H and $^{13}$C NMR, 17 was identified as soyasapogenol B monoglucuronoid (Taniyama et al., 1988).

Example 16

Acid Hydrolysis of 13 and 14

A 5 mg quantity of each compound was refluxed with 1 mL 2 M HCl in 60% aqueous dioxane (5 mL) for 2 h. The reaction mixture was evaporated, and the hydrolysate after dilution with water (10 mL) was extracted with ether (3×10 mL). The ether extracts were evaporated to afford the aglycons, which were identified as soysapogenol B (m/z $C_{30}H_{50}O_3$ by EIMS) (Hosny and Rosazza, 1999; Taniyama et al., 1988; Kitagawa et al., 1984). The aqueous layer was neutralized with $Ag_2CO_3$ and filtered, and the filtrate was concentrated under reduced pressure. The residue was compared with standard sugars by cellulose TLC [pyridine-EtOAc-HOAc-H$_2$O, 36:36:7:21)] which indicated the sugars to be glucuronic acid, galactose, rhamnose and arabinose in 13 and glucuronic acid, galactose, rhamnose and glucose in 14.

\* \* \*

All of the compositions and methods disclosed and claimed herein can be made and executed without undue experimentation in light of the present disclosure. While the compositions and methods of this invention have been described in terms of illustrative embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,070,623
U.S. Pat. No. 3,070,624
U.S. Pat. No. 4,196,265
U.S. Pat. No. 4,367,110
U.S. Pat. No. 4,452,901
U.S. Pat. No. 4,526,714
U.S. Pat. No. 4,975,369
U.S. Pat. No. 5,049,388
U.S. Pat. No. 5,183,756
U.S. Pat. No. 5,221,605
U.S. Pat. No. 5,238,808
U.S. Pat. No. 5,242,813
U.S. Pat. No. 5,310,687
U.S. Pat. No. 5,607,915
Adlercreutz et al., *J. Nutr.*, 125:757s–770s, 1995.
Agrawal, *Carbon-13 NMR of Flavonoids*; Elsevier Science: NY, 39:192–211, 1989.
Akiyama et al., *J. Biol. Chem.*, 262:5592–5595, 1987.
Arao et al., *Chem. Pharm. Bull.*, 45:362–366, 1997.
Arnon, et al., *Proc. Natl. Acad. Sci.* (USA) 77:6769–6772 1980.
Belgian Patent No. 753773
Brinkmann et al., *Proc. Natl. Acad. Sci., USA*, 88(19): 8616–8620, 1991.
British Patent No. 1346871
Burchell et al., *J. Immunol.*, 131(1):508–513, 1983.
Chang et al., *J. Agric. Food Chem.*, 42:1869–1871, 1994.
Cheeke, *Can. J. Animal Sci.*, 51:621–632, 1971.
Choi et al., *Int. J. Oncol.*, 13:391–396, 1998.
Colcher et al., *Cancer Res.*, 47:1185 and 4218, 1987.
Davis and Preston *Analytical Biochemistry*, 116(2):402–407, 1981.
De Tommasi et al., *J. Nat. Prod.*, 61:323–327, 1998.
Dillman et al., *Antibody Immunocon. Radiopharm.*, 1:65–77, 1988.
Doll et al, *Lancet* 1:793, 1962.
Farmakalidis and Murphy, *Agric. Food Chem.*, 33:385–389, 1985.
Gefter et al., *Somatic Cell Genet.*, 3: 231–236, 1977.
Ghose et al., *CRC Critical Reviews in Therapeutic Drug Carrier Systems*, 3:262–359, 1987.
Ghose, et al., *Meth. Enzymology*, 93:280–333, 1983.
Goding, 1986, In: *Monoclonal Antibodies: Principles and Practice*, 2d ed., Academic Press, Orlando, Fla., pp. 60–61, and 71–74, 1986.
Goren et al, *Planta Medica*, 82: 419–422, 1996.
Harborne et al, *The Flavonoids*; Academic Press: NY, PT2: 756–761, 1975.
Harlow and Lane, Antibodies: A Laboratory manual, Cold Spring Harbor Laboratory, 1988.
Hawrylewicz et al, *J. Nutr.*, 125:698s–708s, 1995.
Heinonen et al, *Anal. Biochem.*, 274:211–219, 1999.
Hosny and Rosazza, *J. Nat. Prod.*, 62:853–858, 1999.
Hostettmann et al., "Chemistry and pharmacology of natural products," In Saponins, Cambridge University Press, pp. 1–548, 1995.
Huang et al., *Zhongueo Yaoii Xuebao*, Chemical abstract No. 98100885, 3:286–288, 1982.
Inoue et al., *Chem. Pharm. Bull.* 6) 2:897–901, 1986.
Japanese Patent No. JP-A-44-32798
Jia et al, *J. Nat. Prod.*, 61:1368–1373, 1998.
Jing et al, *Anticancer Res.*, 13: 1049–1054, 1993.
Joannou et al, *J. Steroid Biochem. Molec. Biol*, 54:167–184, 1995.
Kasiwada et al., *J. Org. Chem.*, 57:6946–6953, 1992.
Kimura et al., *Immunogenetics*, 11:373–381, 1983.
Kitagawa et al, *Chem. Pharm. Bull.*, 33:598–608, 1985.
Kitagawa et al, *Yakugaku Zasshi*, 104:162–168, 1984.
Kohler and Milstein, *Eur. J. Immunol.*, 6:511–519, 1976.
Kohler and Milstein, *Nature*, 256:495–497, 1975.

Kong et al., *Phytochemistry*, 33:427–430, 1993.
Lewis et al, *J. Chem., Soc., Perkin Trans.* 1:2481–2484, 1998.
Mabry et al, IN: *The Systematic Identification of Flavonoids*; Springer-Verlag: New York, 1970.
Manabe et al., *J. Lab. Clin. Med.*, 104(3):445–454, 1984.
Martin et al., *J. Exp. Med.*, 182:1545–1556, 1995.
McIntosh et al, *J. Nutr.*, 125:809–816, 1995.
Menon et al, *Nutr. Cancer*, 30:74–77, 1998.
Merz-Demlow et al, *Am. J. Clin. Nutr.*, 71:1462–1469, 2000.
Messina, *Am. J. Clin. Nutr.*, 70:439S–450S, 1999.
Messina et al, *Nutr. Cancer*, 21:113–131, 1994.
Miotti et al., *Cancer Res.*, 65:826, 1985.
Mujoo et al, *Oncogene*, 12:1617–1623, 1996.
Nagamoto et al., *Planta Medica.*, 54:305–307, 1988.
Naik et al, *Anticancer Res.*, 14:2617–2619, 1994.
Naim et al, *J. Agric. Food Chem.*, 24:1174–1177, 1976.
Nikaido, T.; Ohmoto, T.; Kinoshita, T.; Sankawa, U.; Delle Monache, F.; Botta, B.; Tomimori, T.; Miyaichi, Y.; Shirataki, Y.; Yokoe, I.; Komatsu, M. *Chem. Pharm. Bull.* 1989, 37, 1392–1395.
Nwokolo and Smartt, *Food and Feed from Legumes and oilseeds*; Chapman and Hall: London, 90–101, 1996.
Oakenfull et al., *Atherosclerosis*, 48:301 (1983).
Okura et al, *Biochem. Biophys. Res. Commun.*, 157:183–189, 1988.
PCT Application No. WO 91/01750
Peterson and Barnes, *Biochem. Biophys. Res. Commun.*, 179:661–667, 1991.
Pieterez et al., *Antibody Immunoconj. Radiopharm.*, 1:79–103, 35, 1988.
Pisha et al., *Nature Medicine*, 1:1046–1051, 1995.
Pool-Zobel et al, *Carcinogenesis*, 21:1247–1252, 2000.
Rao and Sung, *J. Nutr.*, 125:717S–724S, 1995.
Rao et al, *Cancer Res.*, 57:3717–3722, 1997.
Reisfeld et al., *Melanoma Antigens and Antibodies*, p. 317, 1982.
Remington's Pharmaceutical Sciences, 15th Ed., Chapter 33, 624–652, 1990.
Remington's Pharmaceutical Sciences, 16th Ed. Mack Publishing Company, 1980
Rubinstein et al, *J. Natl. Cancer Inst.*, 82:1113–1118, 1990.
Setchell, *Am. J. Clin. Nutr.*, 68:1333S–1346S, 1998.
Shepard et al., *J. Clin. Immunol.*, 11:117–127, 1991.
Stevenson et al., *Chem. Immunol.*, 48:126–166, 1990.
Talukdar et al, *Phytochemistry*, 53:155–157, 2000.
Taniyama et al, *Yakugaku Zasshi*, 108:562–571, 1988.
Tezuka et al, *J. Agric. Food Chem.*, 48:1111–1117, 2000.
Thompson et al., *Cancer Epidemiol. Biomarker Prevent.*, 1:597–602, 1992.
Thor et al, *Cancer Res.*, 46:3118, 1986.
Tipson and Horton, *Advances in Carbohydrate Chemistry and Biochemistry*. Academic Press: New York, London., 41:27–66, 1983.
Tomas-Barbaren et al., *Planta Medica.*, 54:266–267 (1988).
Vaickus et al., *Cancer Invest.*, 9:195–209, 1991.
Woodson, *Statistical Methods for the Analysis of Biochemical Data. Series in Probability and Mathematical Statistics*; Wiley: N.Y., 315–316, 1987.
Wyllie, *Anticancer Res.*, 5:131–136, 1985.
Yanagihara et al, *Cancer Res.*, 53:5815–5821, 1993.
Zhou et al, *Nutrit.*, 129:1628–1635, 1999.
Zhou et al, *Cancer Res.*, 58:5231–5238, 1998.

What is claimed is:

1. A compound represented by formula (V):

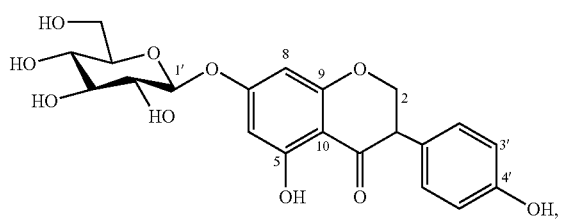

or a pharmaceutically acceptable salt thereof, wherein $R_5$ represents hydroxyl.

2. A pharmaceutical composition comprising, in a pharmacologically acceptable medium, a compound (V)

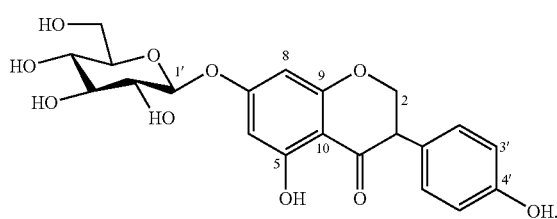

or a pharmaceutically acceptable salt thereof, wherein $R_5$ represents hydroxyl.

3. The pharmaceutical composition of claim 2, wherein said pharmacologically acceptable medium is a buffer, a solvent, a diluent, an inert carrier, an oil, a creme, or an edible material.

4. The pharmaceutical composition of claim 2, wherein said pharmaceutical composition is a tablet, capsule, topical preparation or dietary supplement.

5. A kit comprising the pharmaceutical composition of claim 2 in a container.

* * * * *

UNITED STATES PATENT AND TRADEMARK OFFICE
CERTIFICATE OF CORRECTION

| | | |
|---|---|---|
| PATENT NO. | : 7,112,573 B2 | Page 1 of 1 |
| APPLICATION NO. | : 10/126483 | |
| DATED | : September 26, 2006 | |
| INVENTOR(S) | : John P.N. Rosazza and Mohammed Hosny | |

It is certified that error appears in the above-identified patent and that said Letters Patent is hereby corrected as shown below:

Title page, item (73), "Assignee", please delete "Iowa Research, The University Foundation" and insert --The University of Iowa Research Foundation--.

In claim 1, column 56, beginning on line 26, please delete "wherein $R_5$ represents a hydrogen or hydroxyl".

In claim 2, column 56, beginning on line 41, please delete "wherein $R_5$ represents a hydrogen or hydroxyl".

Signed and Sealed this

Tenth Day of April, 2007

JON W. DUDAS
*Director of the United States Patent and Trademark Office*